(12) United States Patent
    Goel

(10) Patent No.: US 12,565,663 B2
(45) Date of Patent: Mar. 3, 2026

(54) MATRIX ATTACHMENT REGIONS AND USES IN PROMOTING GENE EXPRESSION

(71) Applicant: Celltheon Corporation, Union City, CA (US)

(72) Inventor: Nikhil Goel, Union City, CA (US)

(73) Assignee: Celltheon Corporation, Union City, CA (US)

( * ) Notice: Subject to any disclaimer, the term of this patent is extended or adjusted under 35 U.S.C. 154(b) by 1052 days.

(21) Appl. No.: 17/311,306

(22) PCT Filed: Dec. 6, 2019

(86) PCT No.: PCT/US2019/064910
§ 371 (c)(1),
(2) Date: Jun. 4, 2021

(87) PCT Pub. No.: WO2020/118169
PCT Pub. Date: Jun. 11, 2020

(65) Prior Publication Data

US 2022/0017916 A1     Jan. 20, 2022

Related U.S. Application Data

(60) Provisional application No. 62/776,643, filed on Dec. 7, 2018.

(51) Int. Cl.
C12N 15/85          (2006.01)
(52) U.S. Cl.
CPC .......... C12N 15/85 (2013.01); *C12N 2830/46* (2013.01)
(58) Field of Classification Search
CPC ..... C12N 15/85; C12N 2830/46; C12N 15/64
See application file for complete search history.

(56) References Cited

U.S. PATENT DOCUMENTS

2012/0040460 A1\*   2/2012   Rigoutsos .............. G16B 30/00
                                                    435/375
2018/0187229 A1      7/2018   Mermod et al.

OTHER PUBLICATIONS

Arope et al. Molecular Characterization of a Human Matrix Attachment Region Epigenetic Regulator. PLoS One. Nov. 14, 2013;8(11): e79262. eCollection 2013. (Year: 2013).\*
Price et al. The impact of RNA secondary structure on read start locations on the Illumina sequencing platform. PLoS One. 2017; 12(2): e0173023. Published online Feb. 28, 2017 (Year: 2017).\*
UCSC Genome Browser on Zebrafish Jul. 2010 (Zv9/danRer7) (accessed at: https://genome.ucsc.edu/cgi-bin/hgTracks?db=danRer7 &lastVirtModeType=default&lastVirtModeExtraState= &virtModeType=default&virtMode=0&nonVirtPosition=&position= chr22%3A1%2D42261000&hgsid=2331524680_ MbawdcFIPS34dwkaSMPoOuhFjtaG) (Year: 2010).\*
Recombinant. National Cancer Institute. (accessed at: https://www. cancer.gov/publications/dictionaries/cancer-terms/def/recombinant) (Year: 2024).\*
Transgene. . merriam-webster (accessed at: https://www.merriam-webster.com/dictionary/transgene on May 29, 2025) (Year: 2025).\*
International Search Report for PCT/US2019/64910, International Filing Date Dec. 6, 2019, 6 pages.
Written Opinion of the International Searching Authority for PCT/ US2019/64910, International Filing Date Dec. 6, 2019, Date of mailing Apr. 16, 2020, 7 pages.
GenBank submission CT009593.9, Mar. 24, 2009 [online]. [Retrieved on Apr. 1, 2020). Retrieved from the internet <URL:https://www. ncbi.nlm.nih.gov/nuccore/CT009593 > entire document, nt 70786-70971.

\* cited by examiner

*Primary Examiner* — Marcia S Noble
*Assistant Examiner* — Briana N Ebbinghaus

(57)          ABSTRACT

The present disclosure relates to new identified matrix attachment regions (MAR) and chimeric sequences. Also disclosed are nucleotide constructs containing a MAR at a suitable location relative to a protein-coding sequence for optimal expression of the protein.

2 Claims, 4 Drawing Sheets

Specification includes a Sequence Listing.

SEQUENCE LISTING

```
<160> NUMBER OF SEQ ID NOS: 36

<210> SEQ ID NO 1
<211> LENGTH: 186
<212> TYPE: DNA
<213> ORGANISM: Artificial Sequence
<220> FEATURE:
<223> OTHER INFORMATION: Synthetic

<400> SEQUENCE: 1
aaataattaa ttagcaaata atttatatat ttatatattt atatatatat atatatatat      60
atatatatat atatatatat atatatatat atatatatat atatatatat atatatatat     120
atatatatat atatatatat atatatatat aaatatataa atatatatat atatatatat     180
attggt                                                                186

<210> SEQ ID NO 2
<211> LENGTH: 185
<212> TYPE: DNA
<213> ORGANISM: Artificial Sequence
<220> FEATURE:
<223> OTHER INFORMATION: Synthetic

<400> SEQUENCE: 2
aaatatttca aaaattaagc aaagaaactt tcacagtatg actaataata tttttcttc       60 tggagaaagt cttatttgtc ttatttcggc tagaataaaa acagtttta attttttaaa      120 caccatttta cggacaaaat tattagcccc tttaagctat atttattttc aatagtctac     180
agaac                                                                 185

<210> SEQ ID NO 3
<211> LENGTH: 98
<212> TYPE: DNA
<213> ORGANISM: Artificial Sequence
<220> FEATURE:
<223> OTHER INFORMATION: Synthetic

<400> SEQUENCE: 3
gggagaagca gtccaatgtg gctgtatata tatattatta tttttttttt tttaaataca      60
aacaattaag ctgtcgaact gttgtataaa cacaatat                              98
```

-continued

```
<210> SEQ ID NO 4
<211> LENGTH: 1879
<212> TYPE: DNA
<213> ORGANISM: Artificial Sequence
<220> FEATURE:
<223> OTHER INFORMATION: Synthetic

<400> SEQUENCE: 4
atgcaaagga ctctttctgt aaaatatctg ctgtaaaaat ctaaaggatt tgagggttgc      60
actcccaaag gctcctgaga gcttgtgtaa aataagcctt cctaactgct gctttctcac     120
tttagtcaat tttggccttt tttatattca tatacagtaa atgttgctct aatcaatgtg     180
gatgatcatt atcagtatat gactcgaaaa atattttaaa cttctctttg cttctagacc     240
aggatttgaa ggaatattct attttttaatg acactgcttt gcaatattta tgattcttaa     300
agtcaaacag agtgaaacag aagtaaacat gtcatgatgt acactcacat gaaacaatct     360
ctgaaatgaa gaatgaatga agaaagttgt gttgctaaca aaatggagga agactcacga     420
atagacaaaa gcagggcaga aacgagacac gcacccgtgt acatatatac agttgaagtc     480
agacttatta gcccccccttt gattttttttt tctttttttta aatatttcaa aaattaagca     540
aagaaacttt cacagtatga ctaataatat ttttttcttct ggagaaagtc ttatttgtct     600
tatttcggct agaataaaaa cagtttttaa tttttttaaac accattttac ggacaaaatt     660
attagcccct ttaagctata tttattttca atagtctaca gaacaaataa ttaattagca     720 aataaatttat atatttatat atttatatat atatatatat atatatatat atatatatat     780
atatatatat atatatatat atatatatat atatatatat atatatatat atatatatat     840
atatatatat atataaatat ataaatatat atatatatat atatattggt gggagaagca     900
gtccaatgtg gctgtatata tatattatta tttttttttt tttaaataca aacaattaag     960
ctgtcgaact gttgtataaa cacaatatca ctcgagttgc agtccgatgt gactatatat    1020
tggcactggt gggagatttg cattcattgt gacaatatac agccacattg cattgctacg    1080
agtgtgatat tatgtttata caccagttca acagcataat cgtgtgtaat aaaaagataa    1140
tcaaacacgg aagaggaact actttcttcc gccattcatt cacatctgca gcttacgtca    1200
gaacagcaga agctgttgct cattcatata tataatatat ataaatttgt atacttacag    1260
acgacacagt ggctcagtgg ttagcactgt ctcctcacag caagaaggtc actgtttcaa    1320
gtccaggctg ggtccgccgg catttgtgtg tggagtttgc ttgttttttcc cgtgttaatg    1380 tgtatggatg tttcccagta ctgggttgca gctggaaggg catccgctgt gtaaaactta    1440
tgctggataa gttggcagtt cattccgctg tgtcaacccc tgatgaataa agggattaag    1500
ccaaatgaaa atgaatgaat gatttaatac tcttgtttaa gtcttagtgc cgattatata    1560
tagatatgtg gtgttagatc aaaccagtgt tcattttgac agcaaaattt gatttagttt    1620
tagtcatttt ttagtcttcc atattcgtta tagcatcagt ctatatacag tcaactaaat    1680
taaacatgat tttagtcaac ttcatgcatt ttcacatgga caaggtcatt aaaattctac    1740
aggatcaggt tgtaccaact ctatctcatg gaaatttgta acttttttgat tgtggctaat    1800 tcgtatgaat ttgtatgatc tcatttgtac aatttagtat tatttgctca tccccccagtg    1860 atggttggat ttagggttg                                                 1879

<210> SEQ ID NO 5
<211> LENGTH: 225
<212> TYPE: DNA
<213> ORGANISM: Artificial Sequence
<220> FEATURE:
```

-continued

```
<223> OTHER INFORMATION: Synthetic

<400> SEQUENCE: 5
tatccaaata tatatatata tatatatata tatatactat atatatatat atatatatat        60
atatatatat atatatatat atatatatat atatatatat atatatatat atatatatat       120
atatatatat atatatatat atatatatat atatatatat atatatatat atatatatat       180
atatatatat atatatatat tttttttttt tttttaaga aaaca                        225

<210> SEQ ID NO 6
<211> LENGTH: 106
<212> TYPE: DNA
<213> ORGANISM: Artificial Sequence
<220> FEATURE:
<223> OTHER INFORMATION: Synthetic

<400> SEQUENCE: 6
caaatttgct atacaaaaac ctaaatgtaa taaagttaca tccataaaag tgactttta         60 ttacttttga aacacaacag atttatgccc tgtctatatc cagttc                      106

<210> SEQ ID NO 7
<211> LENGTH: 109
<212> TYPE: DNA
<213> ORGANISM: Artificial Sequence
<220> FEATURE:
<223> OTHER INFORMATION: Synthetic

<400> SEQUENCE: 7
gttataataa ttttataatc tctcacaata ttgctgtttt actgattttt gaataaatgc         60
agccttggtg agcataagag acttttttcta aaaactttga aaagtctta                   109

<210> SEQ ID NO 8
<211> LENGTH: 2679
<212> TYPE: DNA
<213> ORGANISM: Artificial Sequence
<220> FEATURE:
<223> OTHER INFORMATION: Synthetic

<400> SEQUENCE: 8
tgttacatta ggctgaaaac acactgtgta tgtgcatatt ttcccttaaa tacataaaga         60
agtaatgggt ggcgtacctg tattggttat agactccagg gcagtataac atggctgtga        120
atagactctg ttgtggacat acactccata acaccaaact gatcccgtag aacgatgtca        180
ccaggaaaag aaggagcgtc aaaatgaact gcctgtgatt ggcttgacct acacagctgt        240
ttatcctgtc atggaaagtc acatacatac aagacacaaa taataagcaa cacatttaca        300
gatattttca ttcaaacaat ttagaacaat tatactattt tctctcttgt caatgtagct        360
ttaatgagaa ttatgtggct catggcatgt tcatatttat atttgtgcct gtgtgtgtgt        420
tgaagtagca tggagacaga ttggcctggt gagagctccc tttactgtgc tgaaaactgt        480
gttcctgttg cctttgcaca tgtctcacca gcctgcctgc tccagtgacg tctttttggga       540 atcagcttga acatatgtgt gtgtctgatg gggtagggaa cacatgcata caagtgtgaa        600
gagatcagaa aatgaatcaa atcattggca tgaccactaa tttaaacaat tcattttgga        660
attgttcagc tacttctgta gtaaggattt gcaataagcc agatatctta gaaggaaagg        720
cacaaatatc aacattaaaa ttaatatttg aaataacaga aaatatattc ggttgactga        780
ttatccaaca aacacaagtg taaagtgata tttttaatga acatctaaaa ttacaatgca        840
acggtaagtc tgtgaagctg agatgattaa aatgtgatct ttatgaatga aagcagatgg        900
```

```
ccacaatgct ctctctcctt ttattgttta taaatcataa atcatcaatt catatagtaa        960
cttttttaga ttttgaatat ttatttatgt aaagttttaa atattattga atagtaaata       1020
atttaatatg ataatcattt ataaaagtgt atatttgtaa atacaattat ttttaaaata       1080
tataaatgat gaaaaaaatt taaatataag aataaacact tttataaata atacaaggca       1140
aatttgctat acaaaaacct aaatgtaata aagttacatc cataaaagtg acttttatt        1200 acttttgaaa cacaacagat ttatgccctg tctatatcca gttctatcca aatatatata       1260
tatatatata tatatatata ctatatatat atatatatat atatatatat atatatatat       1320
atatatatat atatatatat atatatatat atatatatat atatatatat atatatatat       1380
atatatatat atatatatat atatatatat atatatatat atatatatat atatatatat       1440
atattttttt tttttttttt aagaaaacag ttataataat tttataatct ctcacaatat       1500
tgctgtttta ctgatttttg aataaatgca gccttggtga gcataagaga ctttttctaa       1560
aaactttgaa aagtcttacc gacaacatat tattgaatgg cagtgtaaat atagatcgtt       1620
ttgtcattta gagaatattt aattaatgtt taatacactt cacactagga atgaagtgct       1680
cgtactcaat ttttaaagaa gaaggaatga gaaacccacc aaacacagtg gtggtccatt       1740
cgaaggacac atgccccaca gatcctgcag tgccctgccc ttggtgggcg cacctgtcgg       1800
cacacagggc ataacttctt ctttccttcg ttttccccat ttgactgact gattcctttg       1860 caggggggcgg agtctccagg tatgtttgtg ctctgattgg ttgtacagat actgttaatt       1920
ccctgagcta atgactggga tttgacaaag cctggtcctt gtttggtgcg cacaagggag       1980
ataagggtca acatcatgcc tgtcgtcaca gtaaccagct gcagattact gacgtctcct       2040
ctgggaacga tctcagtaag gaaaagatag tacatgtagg caagggagaa aagtgccaag       2100
ctaaggaaaa acaatgtgcg tcttttcctt ctgtgagtca catagtaata ccaaagcacc       2160
agtcctggta gggcagttag gacaacaact cccaacatac agttaattgc tgctactcgc       2220
aacagaccag gaattaatac catgggaggt aagacagaga tttccaatcg aaggggtcct       2280
acggcacaac atggcaaacc caaacgatca gccatacaag agacgaaacg agagaagatg       2340
tctggcttgt cttgctctcc tctgactaac ctattgagaa agagtgacaa attccaccat       2400
catcatttac acactattat gttatcagtt ttatgtatgg aaatgacaag gtgcaaacgg       2460
acaaaattat ttaattcaac tacactttt aaagtgtaaa aatgtaaagt gtcaaaagtt       2520
tatatcaata aatgtaatgt aaaaccatct ctgcatgcca tgatcttaac tggttgacct       2580
ctgacctttc acaggcatca tctagttctt cacagtcaca gcagcagtac tctctttgct       2640
ggtcgatgtc tccacagcag cacagagggt catctggtt                              2679
```

```
<210> SEQ ID NO 9
<211> LENGTH: 350
<212> TYPE: DNA
<213> ORGANISM: Artificial Sequence
<220> FEATURE:
<223> OTHER INFORMATION: Synthetic

<400> SEQUENCE: 9
atatatatat gttagtgata tatatataaa atatatatca ctcttattat atattatata         60
tattatataa tatataatat attatattat ataatatatt atatattata taatatatat        120
aatatattat atattatata atataatata ttatatatta tataataata taatatatta        180
tatattatat aataatatat aatatattat ataataatat ataataatat ataatatatt        240
```

-continued

```
attatataat atataataat atataataat ataataatgt gattatatta tatataatat      300
gtaatataat aatgtatata tattatatat gcattatata taatgatttt                 350

<210> SEQ ID NO 10
<211> LENGTH: 186
<212> TYPE: DNA
<213> ORGANISM: Artificial Sequence
<220> FEATURE:
<223> OTHER INFORMATION: Synthetic

<400> SEQUENCE: 10
aattgcataa gccaatccct tgcaataaat aaaatagatc gagatgtaga tagacagaga       60
tccagatcct actggttcca tttttcctggc agaaccatga tggatatgat atatgtccca     120
taaagagcct cccagtggtg tcttttttgtt ttgtaaagat ggtttttaatc cacagattta    180 agagtg                                                                 186

<210> SEQ ID NO 11
<211> LENGTH: 153
<212> TYPE: DNA
<213> ORGANISM: Artificial Sequence
<220> FEATURE:
<223> OTHER INFORMATION: Synthetic

<400> SEQUENCE: 11
ctatcaaatg tatatttaaa tctacctact tgtgttatat atttatatat gtgtgtgtga       60
tatgtataat tttaaaatat atctgtatag ctacttaatt tgtatttcca gcccaattca      120
gtctagtgac agaaaatata actcatcaag tct                                   153

<210> SEQ ID NO 12
<211> LENGTH: 4061
<212> TYPE: DNA
<213> ORGANISM: Artificial Sequence
<220> FEATURE:
<223> OTHER INFORMATION: Synthetic

<400> SEQUENCE: 12
tacccagtaa ttcttaaact acttactcca gcacttggcc catggcaaat ttcctggtag        60
ccatatgtac atatacacat gctttttaaat acataaacgt atgtacatat actttttaatt     120 tactactaag attttataca tttttccagta gtttgtatga tgaacatgta tatacctccc     180
tttaaagtta aacaataaaa aaatcttaat ttttctacct taaaatctcc tctcatcacg      240
tcatccaatg atagccgctg ttaacatcat gttcctattt acttctgctt gtttctctga      300
agatgtacgt gagtgggtaa acacgatgta atttgacatt gcggttttta atagcatatc      360
acaaatattt tcctgttata atttcattca caaacatggt tctgatagtt acataatatt      420
acaccatatg atcatttcct agtttactta gctatttcct atggttggat attcttggct      480
tgtttccaat attttttctat tctaattcat ctccaacaaa agtcatcatc tgtgaatctt      540
tctctgcatc tctaagtatt tccttagaat aaactcctag agtgaatctg ttagcacatt      600
tgtttctctc ttttaattaa caactggaaa atgattattg cagacacatt ctcttcaagt      660
gaatatttct tctcggctga actttgcttt actgagtatt tttccctccc ttggctgcat      720
tttcattctt cttttgctgt tttgcgtttc actcccacct acaaaatatc caagttccct      780
ctcccaaaat aaaacccctc ttggttcatg gcagagtcaa ctttgttcag ctgtctttac      840
cctgcaggtc caaaggtcta ttgcccagag tatttgctga ggggataaga ggtgccaggt      900
cctcatcaga gtaatctttg catcttccat tttagatgat gaggctgagg ctaaataact      960
```

```
ttttgtgact tgaacaaaat cacgcccgtc attttggagc agagattgga cccagaccat    1020
ctgactgcag tgcacttggt tactacacaa cagccctgga agctgcaacc tgaggacctc    1080
cagcctcaca tgaatcatct tcatccacca accttctccc atctgggttc ccacactcct    1140
cccatcaccc agcatggggg gcctcatggt ggtggttgac ccttcctcta tctccacctg    1200
catatggggc acattctccc caaacctcac tccagtccaa tctcacctca accccactgt    1260
ctcgctcata gggttgagga aagacagaat aaaccctggc tgggaaaagt cactttagtc    1320
aatgtacggt cagttttacg tgtcagcttg gccaggctag agtccccagt catccaaacg    1380
cccagttgac tgtaagcaaa gactatccta gataatttgg tcggcctgag acattcagtt    1440
aaaagaccat aagagcagaa ctgaaaacag aaaattctgc ctgtggactg cagcgccagc    1500
tcctgcctga gagtttccag cctgaccttc ctaaacttgc ctactaatcc cccacaattg    1560
cataagccaa tcccttgcaa taaataaaat agatcgagat gtagatagac agagatccag    1620
atcctactgg ttccattttc ctggcagaac catgatggat atgatatatg tcccataaag    1680
agcctcccag tggtgtcttt ttgtttttgta aagatggttt taatccacag atttaagagt    1740
gatatatata tgttagtgat atatatataa aatatatatc actcttatta tatattatat    1800
atattatata atatataata tattatatta tataatatat tatatattat ataatatata    1860
taatatatta tatattatat aatataatat attatatatt atataataat ataatatatt    1920
atatattata taataatata taatatatta tataataata tataataata tataatatat    1980
tattatataa tatataataa tatataataa tataataatg tgattatatt atatataata    2040
tgtaatataa taatgtatat atattatata tgcattatat ataatgattt tctatcaaat    2100
gtatatttaa atctacctac ttgtgttata tatttatata tgtgtgtgtg atatgtataa    2160
ttttaaaata tatctgtata gctacttaat ttgtatttcc agcccaattc agtctagtga    2220
cagaaaatat aactcatcaa gtctgggtaa tctcaaataa ttcggctaaa ttcctcaatt    2280
catcaatttc tccctcctcc agcctccgca taattgattc taactttcag ggagttgaag    2340
cagcactgcc ctgggggggct ctcttccagc tctcagcccc tccctgcaca gctctggtgc    2400
ccacggggat gcgcccacgg ggatgcaagg ccctgtatga ccatcagacc tcctgtcctc    2460
acttgagatg tttatttcta gtccccagtc ctgccccaac cacaggatgt aacccagacc    2520
ctggtctcta ttccaagatt catccttgtc aagcggttct cagcagcatg cctctgccac    2580
gcccagtcac agaggacgat attggctccc ctctttatgg ggggaggata aaaaggatca    2640 tatcccgac ccctgggctt aaggcttcca tgttcccatc tctactcttt aatgccagga    2700
tgacataggg tactttctgc aggcatagac aaccaggcag gaagaggggc ccatgttcct    2760
tgtaatctca gatcacaagt accctctggg gatctatcac cccaagcttg gtgcatggac    2820
aaggggtacc ttattctctt cctttcttct aagactatgc actgcctctc ccccaggcaa    2880
atggaatctt gtcaattcca agtgagtttg gaaaaactca ttctttttta cttattgttt    2940
agatcggaac ctaaaatcga aagttccagg aagctcaagt tcttataact aaaaaggctt    3000
ttctctctca agagcattgg ctctgtcttt tccatgttct actttgaaac acaaaagctg    3060
agctcgacat tgatttaatt gctttttatt tgaatgattc ctataagtga cacctttttgg    3120 ggcagtatgt cctagctggt tgaattagag ttgggaaaca cattgcaaga aagggtagaa    3180
agaggcatac tttattgaat cttttggagt aactttttgtg cctgttacca caagcttatt    3240
tttgataaga tgcttcctaa ctttcctcgc tcacccctac ctcatctcag ggccaagcac    3300
```

-continued

```
gaaagttgtt ttatacatgc taggtttggc tgatttcaat gtgacttccc caggggcagaa       3360 gagacagtgg ttgaaggatg aagaatcaac ctacccgggg gaatcaaaga ttgatcccag       3420
ggaatggagc agatataatt aaataagttt tttctttccc cagtgtatct aatattcatt       3480
tttgtattta cttggagcaa atgaatttaa atgaattttt agttagagtt aaatcaactc       3540
attaaaacac attgaaggaa ttagaaatgt aaaatcattt cctgctgcaa ttcattcatc       3600
tctaagtcta taactgactt gaatctaggt aaaggtcatt gcttaaaggg gacagtggcc       3660
cttattcttg caacctacaa acttttacag tttgcatgga gttttcacat ccatgaactc       3720
aagcaagact gaataggcct gtatggtgaa caaacaggag taaatgcctc cactattcag       3780
gggaggaaag tgagctcaaa aaagtttaat attgttgcct aaggatactc aaccagcaaa       3840
tggcaatatc gagacaggag caggtcttca gtccaaaccc acagagcaga gcttgcccag       3900
gaagctgatc attcttgtac caccttctcc atcactggac ctacaccctg cccttcttta       3960
cccagctctg acctctcaga tgctgaacct ggggtgccct tgtcattgaa cttcgagttg       4020
cattattttc ccattgtttt acctacaatt aacttgccgt c                           4061
```

```
<210> SEQ ID NO 13
<211> LENGTH: 1700
<212> TYPE: DNA
<213> ORGANISM: Artificial Sequence
<220> FEATURE:
<223> OTHER INFORMATION: Synthetic

<400> SEQUENCE: 13
agactctgtc tcaaatatat atatatttat atatatatat tttatattta atatatataa         60
tatatattat atataaattt attatatata atatatatta tatataaatt tattatatat        120
aatatatatt atatatatta tatgttatat atatttatta catataatat ataatatata        180
tttattatat ataatatata tttattatat attatatatt atatattta tattttatat        240 atattatata attttatatt ttatatatat tatataatta atatttaata tatattatat        300
atatatatat aatatatatt tattatatat aatatatatt tattatatat tatatattat        360
atatttatat tttatatata ttatatattt atatttata tatattatat atttatattt        420
tatatatatt atatataata tatatattat atattttata tataatatat atttattata        480
catattttat attatatata atatatattt attatatatt tttatatata ttatatataa        540
tatatatata tttatatata tatattttat atttaatata tataatatat attatatata        600
aatttattat atataatata tattatatat aaatttatta tatataatat atattatata        660
tattatatgt tatatatatt tattacatat aatatataat atatatttat tatatataat        720
atatatttat tatatattat atattatata tttatatttt atatatatta tatatttata        780
ttttatatat attatatatt tatatttat atatattata tataatatat atattatatc        840
ttttatatat aatatatatt tattatacat attttatatt atatataata tatatattat        900
atatatatat atatatatat ttatatatat atatatttat atatttata tatatataat        960 atatattaat tatatataat atatatatta tatatatatt atatataata cgtaatatat       1020
atttattata tatattttgt atatattata tattatatat ttattatata tattttatat       1080
atattatgta tattttatat acaatacata atatatattt tatatacaat atataatata       1140
tattttatat acaatatata atatatattt tatataatat attttttatat aatatatatt       1200 ttatattata tataatatat attttatata ttatatataa tatatatttt atattatata       1260
taatatatat tttatactat atataatata tattttatac attatataat atatatttta       1320
```

```
tactatatat aatatatatt ttatacatta tataatatat attttatata ttatataata    1380
tatattttat gttatataat atatatttta tgtattatat aacatatatt ttatgtatta    1440
tataacgtat attttatata ttatgtaacg tatattttat atattatgta acgtatattt    1500
tatatattat gtaacgtata ttttatatat tatgtaatat atatttttata tattatatat    1560 tttgtatatt atatattttg tatatgatat attatatatt ttatatatta tatattatat    1620
attttgtata ttatatatta tatattttat atataatata tcatatatat tttatatata    1680
tataaagcat cagtaaacaa                                                 1700

<210> SEQ ID NO 14
<211> LENGTH: 177
<212> TYPE: DNA
<213> ORGANISM: Artificial Sequence
<220> FEATURE:
<223> OTHER INFORMATION: Synthetic

<400> SEQUENCE: 14
taacatggtg aaatatcatc tctactaaaa atacaaaaaa ttagccaggc gtggtggcgg     60
gcgcctgtgg tcccagctac ttgggaggct gagggaggag aatggcgtga acccaggagg    120
catagcttgc agtgagccga gattgcacca ctgcactcca gcctgggcaa cagagca      177

<210> SEQ ID NO 15
<211> LENGTH: 249
<212> TYPE: DNA
<213> ORGANISM: Artificial Sequence
<220> FEATURE:
<223> OTHER INFORMATION: Synthetic

<400> SEQUENCE: 15
ctctagagcc aggcaccgtg actcactcct gtgatcccag cttttcgaaa ggctgaggca     60
ggaggatcgc ttgaggccag gagttcaaga ccagccttgg caacatagtg agactctccc    120
gtctctaaaa caacaacaac aaaaggttaa ttaaaaatta aaagaaaaga aaactccaca    180
gccaccttct ccaggaaaat aagtcccaaa gccacttgcc actgatgcag aggtgcgcag    240
agcccgagg                                                            249

<210> SEQ ID NO 16
<211> LENGTH: 5274
<212> TYPE: DNA
<213> ORGANISM: Artificial Sequence
<220> FEATURE:
<223> OTHER INFORMATION: Synthetic

<400> SEQUENCE: 16
gacagatggg attattcatt tttataaaat atttaaccca acaaatccaa aatatcattt     60
cagcatgtaa ataatacaga tggtccccaa tttaaccatg gttccattaa aggattttttt    120 ttgactttaa taatggattt atcagaatat aacctcatca taagttgagg aacatctgta    180
taaaaatata ttaatgagat accctacatt cattatcctt tgtataccaa gtcttaccat    240
gtggattttg cacttcccac acatctcaat atggaccagc catatcacgt gcccctgcc     300 agatgcatct agtggctttc acatcggaca gctccacact agaatgacag taaggcacag    360
aaccagacag tcccccgct tccagctcct gatcaaccac ttgtagccat gggagctttg     420
gagactgcct taatagttat gaatctaagc taggtgtcat ggctcacacc tgtaatccca    480
actctttggg acgccaagat ggatggatag cttgaggctt ttttttttttt tttttttttt    540
```

-continued

```
tttagacaag agtctcgctc tgttgccagg ctggagtgca gtggcacgat cttggctcac        600
tgcaacctcc gcctcccagg ttcaagggat tctcctgcct cagcctcccc ctgagtagct        660
gagactacag gtgcgcacca ccacgcccag ctaatttttg tattttttagt agagacagag       720 tttcaccatg ttggccagaa tggtctcgat cacttgacct catgatccac ccacctcagc        780
ctcacaaagt gctgggatta caggcgtgag ccaccgcgcc cggccagctt gacgcttgag        840
tccaggaatt caagaccagc ctgggcaaca tggtcgaaac cctgtctcta ctgaaaaaaa        900 aaaaaaaaa ttatccgggc atggtgacac acgcctacag tcccagctac cccagaggct        960
gaggtgggag gatcattgaa cccctaaaag tcaaggctga agtgatccaa gattgcatca       1020
ctgaactcca gtctgggtga tgggagtgag accctgtctc aaaaaaaaaa aaaaatagaa       1080
aagctctgaa tctatgggtt ctagccctgg gaaattctgg ataacatgga gttaacagtt       1140
cacctgcctc aggtgagata atgtaaaact agaaaggtcc ataccattgt gatgtctaat       1200
tgaatctatt tatcaaaaca gtacccaaat gcagtatgtt cagaaacctt atactgttag       1260
gtaataataa ccataaacaa gataaaaaat atgggctggg tgtggtggct cccactgtta       1320
tcctagcatt ttgggaggcg aaggcaggag gatcacttga ggctgggagt ttgagaacaa       1380
cctgggcaac atagcaagac cccatctcta taaaaaaaca tataaatata atataaagat       1440
atatatattt tatatatata catatatttg tacctgttaa cgtggggtga ggggtgcagg       1500
gagggtggaa aggagaaagt cataatatta agcatcagta ggccgggcgc agtggctcat       1560
gcctgtaatc ccagcacttt gggaggctga ggcgggcaga tcacaaggtc aggagattga       1620
gatcatcctg gctaacatgg tgaaatatca tctctactaa aaatacaaaa aattagccag       1680
gcgtggtggc gggcgcctgt ggtcccagct acttgggagg ctgagggagg agaatggcgt       1740
gaacccagga ggcatagctt gcagtgagcc gagattgcac cactgcactc cagcctgggc       1800
aacagagcaa gactctgtct caaatatata tatatttata tatatatatt ttatatttaa       1860
tatatataat atatattata tataaattta ttatatataa tatatattat atataaattt       1920
attatatata atatatatta tatatattat atgttatata tatttattac atataatata       1980
taatatatat ttattatata taatatatat ttattatata ttatatatta tatattttat       2040 atttttatata tattatataa ttttatattt tatatatatt atataattaa tatttaatat      2100
atattatata tatatatata atatatattt attatatata atatatattt attatatatt       2160
atatattata tatttatatt ttatatatat tatatatttta tattttatat atattatata      2220
tttatatttt atatatatta tatataatat atatattata tattttatat ataatatata       2280
tttattatac atattttata ttatatataa tatatattta ttatatattt ttatatatat       2340
tatatataat atatatatat ttatatatat atattttata tttaatatat ataatatata       2400
ttatatataa atttattata tataatatat attatatata aatttattat atataatata       2460
tattatatat attatatgtt atatatattt attacatata atatataata tatatttatt       2520
atatataata tatatttatt atatattata tattatatat ttatattttta tatatattat      2580 atatttatat tttatatata ttatatattt atatttttata tatattatat ataatatata      2640
tattatatct tttatatata atatatattt attatacata ttttatatta tatataatat       2700
atatattata tatatatata tatatatatt tatatatata tatatttata tattttatat       2760
atatataata tatattaatt atatataata tatatattat atatatatta tatataatac       2820
gtaatatata tttattatat atattttgta tatattatat attatatatt tattatatat        2880
attttatata tattatgtat attttatata caatacataa tatatatttt atatacaata       2940
```

```
tataatatat atttttatata caatatataa tatatatttt atataatata ttttttatata      3000 atatatattt tatattatat ataatatata ttttatatat tatatataat atatattta        3060 tattatatat aatatatatt ttatactata tataatatat atttttataca ttatatataata    3120 tatattttat actatatata atatatattt tatacattat ataatatata ttttatatat       3180 tatataaatat atattttatg ttatataata tatattttat gtattatata acatatattt      3240
tatgtattat ataacgtata ttttatatat tatgtaacgt atattttata tattatgtaa       3300
cgtatatttt atatattatg taacgtatat tttatatatt atgtaatata tatttttatat      3360 attatatatt ttgtatatta tatattttgt atatgatata ttatatattt tatatattat      3420
atattatata ttttgtatat tatatattat atattttata tataatatat catatatatt      3480
ttatatatat ataaagcatc agtaaacaac tctagagcca ggcaccgtga ctcactcctg       3540
tgatcccagc ttttcgaaag gctgaggcag gaggatcgct tgaggccagg agttcaagac       3600
cagccttggc aacatagtga gactctcccg tctctaaaac aacaacaaca aaaggttaat       3660
taaaaattaa aagaaaagaa aactccacag ccaccttctc caggaaaata agtcccaaag       3720
ccacttgcca ctgatgcaga ggtgcgcaga gcccgaggaa cacggagtca tagcagctct       3780
gcaaattgat tttattccag gctaaaagat gctatttctc aaaaaaagga gctgggagcg       3840
tctctgttca tgaattcatt tttcagggggt ggggtgattt caagagtcca ggctgtttcc     3900
tgaccatgca cactgttccg gcctggaagc ctcagacccc agccaggctg accacgagcc       3960
agacccggag taagcttcgt cccatgcttc ctgtcggtcc gggcagcctg agtttcctgg       4020
tgacccttcc ctgcacccag ccaattcaaa ggtctggcaa ggcctggtgc cagccaagaa       4080
aatctgaggc agccaggttt gttatttcaa atctctaaac cttcagacct ctgtgcttgg       4140
cttacatatg tgaaagttaa aacaaggatg tgtgtcgcag tggtgattat aattcaagta      4200
agcaaagatc cctgcatgac cagccttcga atgtcagccc atgctgaagt taacacattt       4260
aactcataga acaaaatagt taaaatgagg agtggatgca aaatggtact gccattctag       4320
aaaacagttg gcagtttctt ataaagttaa acgtacgctt accacaagac ccagcaatca      4380
ccctcccaga gaaatgaaaa tttatgttca tataaaatat tgtacacaaa taattataac       4440
agctttattt gtaatagtca tgtatcaatc aggattctcc aaggaaacag gaccaataga      4500
agagagatat atacataata aatcatatat ataaatgata tatataagaa gttatatata      4560
tatacacaaa cacatacata tattgtgata acctaccttg ttttaacctg agtgactctc       4620
tcctagcaga gagagccaga cagactccat tttagtttct tcattcacag ccccctttat       4680
cccccttaag ggaataacta gtgcaagctg actctaagca catccagtaa tgcacctgct       4740
gataagatat tgaggcaggc tgtaccagca gctcctggga atgtgctcgg tggaaggtat       4800
ctaaaagccc ctgcatttat ctcttagtga tagtttaagc ccctgcacct ggaactgttt      4860
atcttttaca actgcttcta taaccaatta attttttaac tttttgcctg ttctgcttct       4920
gtaaaactgc ttcagttaaa ctcccctcc cctatttaga ccatagtata aaagagaatc       4980 tagcccttc ttcggggctg agagaatttt gagtgctagc tgtctctcag tcgccggcta       5040
ataaaggact ccataatttg tctcaaagtg tggcgtttct ctataactcg cttggttaca      5100
acactatctc tcagggatct ccaaagaaat agaacctata ggatatatct atctataata      5160
aatcattgcc aggcatggtg gctcacccag tactttggga ggccaagtca ggaggatcac       5220
ttgagcccag gagtttgagg ccacctgagc aacatagtga gaccctgtct ctac             5274
```

```
<210> SEQ ID NO 17
<211> LENGTH: 965
<212> TYPE: DNA
<213> ORGANISM: Artificial Sequence
<220> FEATURE:
<223> OTHER INFORMATION: Synthetic

<400> SEQUENCE: 17
ccagctactc gggaggctga ggcaggagaa cggcttgaac ccaggaggtg gaggttgcag      60
tgagctgaga tcgcgccact gcactccagc ctgggcgaca gagcgagact ctgtctcaaa     120
aaaaaaatat atatatatat atatatacac atatatatat aaaatatata tatatacaca     180
catatatata taaaatatat atatatacac acatatatat aaaatatata tatatacaca     240
catatatata aaatatatat atacacacat atatataaaa tatatatata cacacatata     300
tataaaatat atatatacac acatatatat aaaatatata tatacacaca tatatataaa     360
atatatatat acacacatat atataaaata tatatataca cacatatata taaaatatat     420
atatacacac atatatataa aatatatata tacacacata tatataaaat atatatatac     480
acacatatat ataaaatata tatatacaca catatataaa atatatatat acacacatat     540
ataaaatata tatatacaca tatatataaa atatatatat acacatatat ataaaatata     600
tatacacaca tatatataaa atatatatat acacacatat atataaaata tatatataca     660
catatatata aaatatatat atacacatat atataaaata tatatatata cacatatata     720
taaaatatat atacacacat atatataaag tatatatata cacacatata tataaaatat     780
atatatacac atatatataa aatatatata tacacatata tataaaatat atatatacac     840
atatatataa aaatatatat atatatttttt taaaatattc caattgtctc actttgtgga     900
tgagaaaaag aagtagttag aggtcaagta acttggccta catctttttct caagattgta     960 aactc                                                                 965

<210> SEQ ID NO 18
<211> LENGTH: 256
<212> TYPE: DNA
<213> ORGANISM: Artificial Sequence
<220> FEATURE:
<223> OTHER INFORMATION: Synthetic

<400> SEQUENCE: 18
ctgtgctccc ttaacatcct attttatctg tatatatata tattcttcca aatatccatg      60
ggaaaaaaaa tctgatcata aaaatatttt aggctgggag tggtggctca cgcctgtaat     120
cccagcactt tgggaggctg aggtgggcgg atcatgaggt caagagatcg agaccatcct     180
gaccaatatg gtgaaacccc atctctacta aagatacaaa actattagct ggacgtggtg     240
gcacgtgcct gtagtc                                                     256

<210> SEQ ID NO 19
<211> LENGTH: 240
<212> TYPE: DNA
<213> ORGANISM: Artificial Sequence
<220> FEATURE:
<223> OTHER INFORMATION: Synthetic

<400> SEQUENCE: 19
ctagtgagca ataaccacat cttcattttc tttgtataaa acaagaaagt ttagcatgaa      60
aaaggtactc aattacaaat gtgttggatt gaattgaaga cccttggaag gggattttgt     120
acctgaggat ctcttttcttt tggccatatt gttcaatgga caaaatttag ccttcgaagg     180
```

```
caggccgatt tgaggttaat actacccttta ccacttgata gctatgtgac cttggccatg     240

<210> SEQ ID NO 20
<211> LENGTH: 3612
<212> TYPE: DNA
<213> ORGANISM: Artificial Sequence
<220> FEATURE:
<223> OTHER INFORMATION: Synthetic

<400> SEQUENCE: 20
gactctagat tataccaacc tcataaaata agagcatata taaaagcaaa tgctcttatc      60
ttgcagatcc ctgaactgag gaggcaagat cagtttggca gttgaagcag ctggaatctg     120
caattcagag aatctaagaa aagacaaccc tgaagagaga gacccagaaa cctagcagga     180
gtttctccaa acattcaagg ctgagggata aatgttacat gcacagggtg agcctccaga     240
ggcttgtcca ttagcaactg ctacagtttc attatctcag ggatcacaga ttgtgctacc     300
tattgcctac catctgaaaa cagttgcttc ctatatttca tccagtttaa tatttattta     360
aaccaagaag gttaatctgg caccagctat tccgttgtga gtggatgtga aagtaccaat     420
tccattctgt tttactatta actatccttt gccttaatat gtatcagtag gtggcttgtt     480
gctaggaaat attaaatgaa tggcatgttt cataggttgt gtttaaagtt gttttttgag     540
ttaaatcttt ctttaataat actttctgat gtcaaaaaca cttagaagtc atggtgttga     600
acatctatat agggttggat ctaaaatagc ttcttaacct ttcctaacca ctgtttttgt     660
ttgtttgttt ttaactaagc atccagtttg ggaaattctg aattagggga atcataaaag     720
gtttcatttt agctgggcca cataaggaaa gtaagatatc aaattgtaaa aatcgttaag     780
aacttctatc ccatctgaag tgtgggttag gtgcctcttc tctgtgctcc cttaacatcc     840
tattttatct gtatatatat atattcttcc aaatatccat gggaaaaaaa atctgatcat     900
aaaaatattt taggctggga gtggtggctc acgcctgtaa tcccagcact ttgggaggct     960
gaggtgggcg gatcatgagg tcaagagatc gagaccatcc tgaccaatat ggtgaaaccc    1020
catctctact aaagatacaa aactattagc tggacgtggt ggcacgtgcc tgtagtccca    1080
gctactcggg aggctgaggc aggagaacgg cttgaaccca ggaggtggag gttgcagtga    1140
gctgagatcg cgccactgca ctccagcctg ggcgacagag cgagactctg tctcaaaaaa    1200
aaaatatata tatatatata tatacacata tatatataaa atatatatat atacacacat    1260
atatatataa aatatatata tatacacaca tatatataaa atatatatat atacacacat    1320
atatataaaa tatatatata cacacatata tataaaatat atatatacac acatatatat    1380
aaaatatata tatacacaca tatatataaa atatatatat acacacatat ataaaaata    1440 tatatataca cacatatata taaaatatat atatacacac atatatataa aatatatata    1500
tacacacata tatataaaat atatatatac acacatatat ataaaatata tatacacaca    1560
catatatata aaatatatat atacacacat atataaaata tatatataca cacatatata    1620
aaatatatat atacacatat atataaaata tatatataca catatatata aaatatatat    1680
acacacatat atataaaata tatatataca cacatatata taaaatatat atatacacat    1740
atatataaaa tatatatata cacatatata taaaatatat atatacacac atatatataa    1800
aatatatata cacacatata tataaagtat atatatacac acatatatat aaaatatata    1860
tatacacata tatataaaat atatatatac acatatatat aaaatatata tatacacata    1920
tatataaaaa tatatatata tatttttaa aatattccaa ttgtctcact ttgtggatga    1980
```

-continued

```
gaaaaagaag tagttagagg tcaagtaact tggcctacat cttttctcaa gattgtaaac   2040
tcctagtgag caataaccac atcttcattt tctttgtata aaacaagaaa gtttagcatg   2100
aaaaaggtac tcaattacaa atgtgttgga ttgaattgaa gacccttgga aggggatttt   2160
gtacctgagg atctctttct tttggccata ttgttcaatg gacaaaattt agccttcgaa   2220
ggcaggccga tttgaggtta atactacctt taccacttga tagctatgtg accttggcca   2280
tgtggtttca acagtctgaa cctcattttc tctgtgtatg tgtggtcctc cttacaagtt   2340
tgtgaaaaat gtgaagtcct tagccatgat agcccaatat aacaggctaa atgataatag   2400
gtttatgttc ttttccttta tattctcaga taagcactgt ccaagtttga ggtgtttttga  2460 ggtctcgcct gatttggatt gtttgagttt atgctattct ttgaattctt tgagctgttc   2520
tgaagcagtg tatcatgaac aaaaacatcc ccagttcagt ccaaacccct ggttacatat   2580
cattcttatg ccatgttata accagtttga gagtgttccc tctgttattg catttaagtt   2640
tcagcctcac acagaaattc agcagccaat ttctaagccc taagcataaa atctggggtg   2700 ggggggggg atggcctgaa gagcagcatt atgaatagca ccattataat taatgatctc    2760
tcaggaagat ttacaatcac aggtagcaga taaaacaaat agtactgctt ctgcacttcc   2820
cctcctttta ttcgctatga aattttatgg gaaatcagtc cagtgaaaaa tgtaagctct   2880
taatctttcc cagaaatcct acctcatttg atgaatactt tgagggaatg aattagagca   2940
tttttttctt ttatagtcta cttcgcattt acgaagtgag gacggtagct taggctgcct   3000
ggccaactga tgagaaggtc agaggcattt ttagagacct ctgttgtctt tcattcatgt   3060
tcattttcca caaggcaagt aatttccaac aaatcagtgt cttcattagt aataagatta   3120
ttaacaacaa taatagtcat agtaactatt cagtgagagt ccattatata tcaggcattc   3180
tacaaggtac tttatataca tctgagtaaa cctcacacaa ttctacaggg aggtatttct   3240
atccccattt aacaaataag gaaacgaagt ccaagtaaat taacttgccc aaggtcacac   3300
agatagtacc tggcagaaca ggaatttaaa cctaaatttg tccaactcca aaagcagcct   3360
tctatttgtt ataaatgctg cctctcatta tcacatattt tattattaac aacaacaaac   3420
ataccaatta gcttaagata caatacaacc agataatcat gatgacaaca gtaattgtta   3480
tactattata ataaaataga tgttttgtat gttactataa tcttgaattt gaatagaaat   3540
ttgcatttct gaaagcatgt tcctgtcatc taatatgatt ctgtatctat taaaatagta   3600
ctacatctag ag                                                      3612
```

<210> SEQ ID NO 21
<211> LENGTH: 599
<212> TYPE: DNA
<213> ORGANISM: Artificial Sequence
<220> FEATURE:
<223> OTHER INFORMATION: Synthetic

<400> SEQUENCE: 21

```
atatgtatat atgtatatat gtatatatgt atatatgtat atgtatatat atgtatatat    60
gtatatatgt atatatgtat atatgtatat atgtatatat gtatatatgt atatatgtat   120
atatgtatat atgtatatat gtatatatgt atatatgtat atatgtatat atgtatatat   180
gtatatatgt atatatgtat atatgtatat atgtatatat gtatatatgt atatatgtat   240
atatgtatat atgtatatac gtatatatgc atatacgtat atatgtatat atgtatatat   300
gtatatatgt atatatgtat atatgtatat atgtatatat gtatatatgt atgtatgtat   360
gtatgtatgt atatatgtat atatgtatgt atgtatgtat gtatgtatgt atgtatatat   420
```

```
gtatatatat atgtatgtat gtatgtatgt atgtatgtat atgtgtatat gtgtatatgt      480
gtatatgtgt atatgtgtat atatgtatat atgtatatat gtatatatgt atatgtgtat      540
atgtgtatat gtgtatatat gtatatatgt atatatgtat atatgtatat atataacat       599

<210> SEQ ID NO 22
<211> LENGTH: 205
<212> TYPE: DNA
<213> ORGANISM: Artificial Sequence
<220> FEATURE:
<223> OTHER INFORMATION: Synthetic

<400> SEQUENCE: 22
gctctttcct ttagttaagc ttatgaaata gtgtttctct catgtttcct ctatattctc       60
tcttttgcct tcctgtttct tcctgttgat tccatcccat tggagtgaaa tcttatgatc      120
ttttggcatc aacaaagtga tctgcatcca ataattcca catctcattc catgttgact        180
gtggatctat atatatatat atgta                                            205

<210> SEQ ID NO 23
<211> LENGTH: 352
<212> TYPE: DNA
<213> ORGANISM: Artificial Sequence
<220> FEATURE:
<223> OTHER INFORMATION: Synthetic

<400> SEQUENCE: 23
agtattaaat tatatataca tatataagtg aaatgtcaca atcttctaga acttgctctg        60
tatgtccact taacatggta gagtgagcta tgtcagcatt ttctatttcc tgtgaatcat      120
tctgtgtgtt gccaagaaga aatatgatat attctgaggt tatgaaatga tattttggtc      180
atcatgtttc tcatcctatt ttcatattac ctaaatactt ttgctttaa aattattatt        240 attaataata atataattat ttatacaata atatttaaat aatatatta tttaatataa        300 ttattatatt tcacataaaa gcaatagttc cagtgttaca aattgtaggc aa                352

<210> SEQ ID NO 24
<211> LENGTH: 5460
<212> TYPE: DNA
<213> ORGANISM: Artificial Sequence
<220> FEATURE:
<223> OTHER INFORMATION: Synthetic

<400> SEQUENCE: 24
ctcgaggtct caagataaga atgactgctg taactcaaat ccaccaaagc tatttgtgtt        60
agaatgcttt cctttggtaa taacataata ccacagagtg agtgaatgta tcaagcaaag      120
tactcactca taatctctcc acccaaatga ctttgtcttc taaaattaaa cccttcccag      180
aggcctctcc ccttaatacc atattgggct cttcacactt cttccaacat cgccttccat      240
cctggccctt ccaacctccc ttctgtttgt gctaggaaca gctcaaggcc tcctatctac      300
cacagagtta catggcttgc cccttgccaa cccccagta ccacacagtg agtgcaaaat       360
ctcaccacat tcagaaccca gtcactattc aaatcatatt ttaaccttg cagtactgac        420 tacttttgat tcatctaaac attactgaac tttattctag aaaacattta agaaatttgt      480
agttaggttc atcctttgag accttacatt taatttcttt ctatgtaaac ggaaagcatt      540
gttcagtccc acgctcatta tggcaaccca cttccaagta cttcgtttac tacgtgggct      600
ggaatcatac agttttctgt tgtgcttgtg ggagcagatc cccctaacct ctgctgattt      660
```

```
ttctcaccac ttatcataca tttattacat gcatgcactg ctgtgtgagt ttctaaatac      720
ttgggtagca attctctact attactttaa ttttcctact tgtctgcaaa tacgaaaagt      780
agcttgaaag aacttcagat ctttgttgtt atctgttgca aacactccat ttttctgttg      840
tagcaaaaaa aaaaaaaaag acatccatag ttgtcaatga gaatgcaaga tacatacatt      900
ctgcacctgt gtgctaacat aagtggctgc cctgtgactc agagattgct tgtccttctc      960
ctaagcctat cctttttgt tactttggat acttttgttc aatgaatcca gaaaaagtgt      1020
ttttcagatt caccatgtga ccctcattta aaacctgtaa tcccctatg gttaagttcc      1080 tgcttttgtt tctgtttct ttctttcagt aaaaggaatt gaacccagtc cttccactta      1140
ctatctgagc atatggctct tttagattat gatgttggtg gtgttcattg gtctcaccaa      1200
aatgctaaag aagccttcat cttctacttg tgggtagtct ttacattcat tactgcaagt      1260
ttagtttatg tggtagtacc agatcctttg cttctttga cttcatgcct acctaacagc      1320
gctctttcct ttagttaagc ttatgaaata gtgtttctct catgtttcct ctatattctc      1380
tcttttgcct tcctgtttct tcctgttgat tccatcccat tggagtgaaa tcttatgatc      1440
ttttggcatc aacaaagtga tctgcatcca aataattcca catctcattc catgttgact      1500
gtggatctat atatatatat atgtaatatg tatatatgta tatatgtata tatgtatata      1560
tgtatatatg tatatatgta tatatgtata tatgtatata tgtatatatg tatatatgta      1620
tatatgtata tatgtatata tgtatatatg tatatatgta tatatgtata tatgtatata      1680
tgtatatatg tatatgtata tatgtatata tatgtatata tgtatatatg tatatatgta      1740
tatatgtata tatgtatata tgtatatatg tatatatgta tacgtatata tatgcatata      1800
cgtatatatg tatatatgta tatatgtata tatgtatata tgtatatatg tatatatgta      1860
tatatgtata tatgtatgta tgtatgtatg tatgtatata tgtatatatg tatgtatgta      1920
tgtatgtatg tatgtatgta tatatgtata tatatgtata tgtatgtatg tatgtatgta      1980
tgtatatgtg tatatgtata tatgtgtata tgtgtatatg tgtatatatg tatatatgta      2040
tatatgtata tatgtatatg tgtatatgtg tatatgtgta tatatgtata tatgtatata      2100
tgtatatatg tatatatata acatagtatt aaattatata tacatatata agtgaaatgt      2160
cacaatcttc tagaacttgc tctgtatgtc cacttaacat ggtagagtga gctatgtcag      2220
cattttctat ttcctgtgaa tcattctgtg tgttgccaag aagaaatatg atatattctg      2280
aggttatgaa atgatatttt ggtcatcatg tttctcatcc tattttcata ttacctaaat      2340
acttttgctt ttaaaattat tattattaat aataatataa ttatttatac aataatattt      2400
aaataatata tttatttaat ataattatta tatttcacat aaaagcaata gttccagtgt      2460
tacaaattgt aggcaatggg ctgttctgat tatctaagtt gggcccagga tatgtgctga      2520
atagttaaag cacatgccca gcatgtatga gggtaaaagg atgggtggat gtagtgaccc      2580
atttgtaatt taagccttag caggcagagg tgtgacccat agtgcaaagt acatagtcat      2640
tataaggtca tctatatcac aatctctgga ttagattgat tgaacctgct cagtgaccaa      2700
tgtgttagca atatacagga ggatgataac atcaacgtca gaagacacat tgaagggctt      2760
acaaatagtg cccattact ttaatacaga aaaattcaat gtaccctcta ggcaatttca      2820
acttttagtc tcttggtagg atagtctaca tttagaatgg ctaattcata aattagaaag      2880
cttcttcacc ccctacttt ctggttattt ctctatgaat gtggtaggca tgagttagta      2940
cacatgtttc catgtacatg tgtttctatg tgtctgcatg catatggtag aatgtactca      3000
tattctatgt acagttagaa caatatttat attgtcaaag aaatcaaaag gagtattata      3060
```

-continued

```
agcttcagaa ataaggataa gtttgaaata ttcattgttt tattttttac agtatttttt    3120
cctttgagaa ttctatgtaa agtactttga acatatttgc cttcaactcc tccctcactt    3180
tcaccctctc ttcattcctc cctttccttt ccactcaaag ttgagattcc tttatttatt    3240
tatttatcct tcaaatatca ctggtactat ccacatgatc tcaggattga ggtctgctct    3300
gacgtgtcat cctgctttca tgcaatggcc ttataggtgg aacaacatta tgaactaacc    3360
agtaccccgg agctcttgac tctagctgca tatatatcaa aagatggcct agtcggccat    3420
cactggaaag agaggctcat tggacttgca aactttatat gccccagtac aggggaacac    3480
cagggccaaa aaggggagt gggtgggcag gggagtgggg gtgggtggat atgggggact     3540
tttggtatag cattggaaat gtaaatgagt taaataccta ataaaaaatg gaaaaaaaaa    3600
gtttctaatg tgtgtttcta gaaacttcct ctcttaaagc aacaacatgt ccatgagcaa    3660
tatagaattg aagatcacca tcaaatcctc tttattcctc attgtttcca tcatgtacta    3720
ccagacctct ttaaagtgta gtacagtgtg ttaggaaatg agcagattat cctgggtatg    3780
tgctaaatta gctactgagt caaaatacat tttttgctga acattaagtg tttggtcatt    3840
tctgggcaaa agaaagaaag aaagaaagaa aagaaagaaa gaaaggaagg aaggaaggaa    3900
ggaaggaagg aaggaaggaa agaaggaagg aaagaaaaaa tggatgtaaa ttgttctgac    3960
agcatctgtc tgagtcaggc agtggaatga aggaggaatc ctagaaatg cacaggaaag    4020 cagcccaagg agagtgtggg ctgaaaggca tcatgttaga aacatgcact cgatgacaga    4080
accttgagaa aaaggaactc aagcaaaagc acttatttaa aattgtaaaa cgcactttat    4140
tcatagccat gggggatgtc aatattccaa gcataagaat gatcagtttc caatcactgt    4200
gaacccccaa aacacaaagt gaaaacccac tactttattt gatgagattt ggggttgctc    4260
tattaattta taaaatcaga gtaagacacg atataaatga aacgattgta gttctaaagc    4320
agcggcactt ccctgaacag tgtcattttg acaagtaact gctaacatct tcaggtcaca    4380
gcgactgaag aaaaagtagg gaaagaaggc tggctgtgct gtttgacatt ttcttttctt    4440
atctggtgac atgaagagaa gctctgggtc cccctactct tgttcatata tctgttgctt    4500
ttatgctgca tcctgaggtt tgaagaaatg catttggcac tgagaaaaga tgaggagaga    4560
atgccttgga catggtccta acatgctttg gtactgagaa aagagagcag aggagatgac    4620
atagaatagg agagataatt tggcctattt tggccttcat ctgagtgata gattttactt    4680
aacaaataga aacaaagttt tacttataaa cagaaccaat gacctgtgtc atctctgata    4740
tattgagctt tgaattcagt gaaattatga actaaatata tcactccata attttctaag    4800
agggctattt gtatagtttc agtgatagtg tgacaaagtg taatctaaat ttctaaaaag    4860
taaaataagt agataaaata gtaggtagaa tagtataata atagaataag tataggtatg    4920
gactagaata aatagacaaa atagtagata aaatgctaat gattttgttg acagggtaat    4980
catgaatatt tttattattt agctaaagaa ccaatgttca tgtactcaag aagtgtattg    5040
aggaacttag gaaattagtc tgaacaggtg agagggtgcg ccagagaacc tgacagcttc    5100
tggaacaggc ggaagcacag aggcactgag gcagcaccct gtgtgggccg gggacagccg    5160
gccaccttcc ggaccggagg acaggtgccc gcccggctgg ggaggcgacc taagccacag    5220
cagcagcggt cgccatcttg gtccgggacc cgccgaactt aggaaattag tctgaacagg    5280
tgagagggtg cgccagagaa cctgacagct tctggaacag gcagaagcac agaggcgctg    5340
aggcagcacc ctgtgtgggc cggggacagc cggccacctt ccggaccgga ggacaggtgc    5400
```

```
ccacccggct ggggaggcgg cctaagccac agcagcagcg gtcgccatct tggtcccggg      5460

<210> SEQ ID NO 25
<211> LENGTH: 220
<212> TYPE: DNA
<213> ORGANISM: Artificial Sequence
<220> FEATURE:
<223> OTHER INFORMATION: Synthetic

<400> SEQUENCE: 25
taggcaacag agtgagatca tgtgtcatat atatatatat atatatatat atatatatat        60
atatatacac acacacacac atatatatat acacatatat atacgtatat atatatatgt       120
atatatatac atatatatac atatatatat atacgtatat atatacgtat atatatatca       180
atgtaaatta tttgggaaat ttggtatgaa tagtcttccc                             220

<210> SEQ ID NO 26
<211> LENGTH: 134
<212> TYPE: DNA
<213> ORGANISM: Artificial Sequence
<220> FEATURE:
<223> OTHER INFORMATION: Synthetic

<400> SEQUENCE: 26
aaatacaaaa attagccagg tgtggtggca tgtgcctgta gtcctaccta ctcgggaggc        60
tgaggcacaa gaatcgcttg aatgtgggag gtggaggttg cagtgacctg agatcgtgcc       120
actgcactcc agcc                                                         134

<210> SEQ ID NO 27
<211> LENGTH: 246
<212> TYPE: DNA
<213> ORGANISM: Artificial Sequence
<220> FEATURE:
<223> OTHER INFORMATION: Synthetic

<400> SEQUENCE: 27
tgtgaacaca gatcataaaa tcatatatca agcagacaaa taagtagtag tcacttatat        60
gcttatactt gtaacttaaa gtaaaagaat tacaaaagca tatgacaaag actaatttta       120
agatatccta atttaaattg ttttctaaaa gtgtgtatac cattttacct atcatatgaa       180
taatttagaa acatgtttat aaaattaatg tccaaatcca ttcaaaagtt ttgtaatgca       240
gatcac                                                                  246

<210> SEQ ID NO 28
<211> LENGTH: 3361
<212> TYPE: DNA
<213> ORGANISM: Artificial Sequence
<220> FEATURE:
<223> OTHER INFORMATION: Synthetic

<400> SEQUENCE: 28
agcgccgaat tcgatccctt tataaaacca caatataatg gagtgctata atttcaaaca        60
gtgtttggtc tgctggcaga gtggtcattc taacagcagt cacagtagag tagaaataag       120
actgcagtat atctaaggca aaaagctgag gtttcaggag cttgaaggta aagaggaaga       180
aagaaatggg aatgggaatt ggaaagacaa atatcgttaa gagaaaattg cttttaggag       240
aggggaaaga atctatgtgt acttaagact atggaatcaa tcccatttaa gctgggaaac       300
tagtttcata tataactaat aaattttatt tacagaatat ctatttacct gatctaggct       360
tcaagccaaa gggactgtgt gaaaaaccat cagttctgtc atattcctaa aaaaaaatta       420
```

```
aaaagttaaa aataaataaa taataaaact tcttttcttt caaaataatc aaggtgctta      480
ttcacatcca ttccaatttg gggaaatact tattttccta tgattagcga agagaaaagt      540
aacttgcatt tcaattcaag ttgatacatg tcacttttaa gaggtcaact aatatttgct      600
agttgagcta accatatagg ctttaaatac tttcatagta gaaagaaaat gaaaatcatt      660
agtgaactgt ataaaataga tcatactttt tgaaagaatc agactgaagt ttccgaaaaa      720
aagaagtaag cttcaatgaa aaggtaagtg aatttagcat ttactcagca tctactatgg      780
acttaacacc taacagtaga taatctgaag gcaaacatat ttgtataggg actgcagaat      840
gatagatgat aaatatcatc tcttctattt gaatgaatat tttttcaaat ctttcacaca      900
cagtggtttg ctatggaaag atttgtagta cattaaacaa atctgaagat ggagttagaa      960
agcttaggct atgttttgag cacaacatat aatttctctg tgattgtttc ttcatctttc     1020
aaatgaggtt actgtgaaga ttaaatgaga taactaaatg atgataaaat aatgtaatct     1080
tagcagcacc ttatttaatc tgtgcaacaa ctctgtgaag tgagtagggc tcagcttcag     1140
tcacttctct gccatttatt aactaagata gtttggaaag ttacccatct cttcagctgt     1200
aaaatgatga ggatcatacc tattttatgg ggctgctttt aggtacaaat atacaggcaa     1260
gcactttgtt aatactaaag cattacacca attagtttta ctcttttcca ttcacacatg     1320
aaattaatgt aatcagaatt ctgtagatta cctaaatctt ctgttaacac gtgatatgca     1380
gttcaggtta aatgtcagtt gagttaccaa agcacataca tactcaccac cctatccaaa     1440
tctacaagcc tcccagtttg tcttcactat tttggttaaa ttaatatgaa ttcctagatg     1500
aaaatttcac tgatccaaat gaaataaaaa atatattaca aaactcacac ctgtaatctc     1560
aacattttgg gaggccaagg caggtagatc acttgaggcc aggagttcaa gaccagcctg     1620
atcaacatgg tgaaaccctg tctctactaa aatacaaaaa ttagccaggt gtggtggcat     1680
gtgcctgtag tcctacctac tcgggaggct gaggcacaag aatcgcttga atgtgggagg     1740
tggaggttgc agtgacctga gatcgtgcca ctgcactcca gcctaggcaa cagagtgaga     1800
tcatgtgtca tatatatata tatatatata tatatatata tatatatata cacacacaca     1860
cacatatata tatacacata tatatacgta tatatatata tgtatatata tacatatata     1920
tacatatata tatatacgta tatatatacg tatatatata tcaatgtaaa ttatttggga     1980
aatttggtat gaatagtctt ccctgtgaac acagatcata aaatcatata tcaagcagac     2040
aaataagtag tagtcactta tatgcttata cttgtaactt aaagtaaaag aattacaaaa     2100
gcatatgaca aagactaatt ttaagatatc ctaatttaaa ttgttttcta aaagtgtgta     2160
taccatttta cctatcatat gaataattta gaaacatgtt tataaaatta atgtccaaat     2220
ccattcaaaa gttttgtaat gcagatcacc cacaacaaca aagaatccta gcctattaaa     2280
aaagcaacac cacctacata taatgaaata ttagcagcat ctatgtaacc aaagttacac     2340
agtgaatttg ggccatccaa cactttgagc aaagtgttga attcatcaaa tgaatgtgta     2400
atcatttact tactaatgcc aatacacttt aaggtaatct taagtagaag agatagagtt     2460
tagaattttt taaatttatc tcttgttgta aagcaataga cttgaataaa taaattagaa     2520
gaatcagtca ttcaagccac cagagtattt gatcgagatt tcacaaactc taactttctg     2580
atacccattc tcccaaaaac gtgtaacctc ctgtcgatag gaacaaccca ctgcagggat     2640
gtttctcgtg gaaaaggaa atttcttttg cattggtttc agacctaact ggttacaaga     2700
aaaaccaaag gccattgcac aatgctgaag tacttttttc aaatttaaaa tttgaaagtt     2760
```

```
gttcttaaaa tctatcattt attttaaaat acggatgaat gagaaagcat agatttgata      2820
aagtgaattc ttttctgcaa tctacagaca cttccaaaaa tcactacaga cactacagac      2880
actacagaaa atcataaata aacaagtgct agtatcaata tttttaccaa aaaatggcat      2940
tcttagaatt ttttataggc tagaaggttt gtacaaacta atctgccacg gattttaaaa      3000
tatgagtgaa taaattatat tgcaaaaaaa atcaggttac agagaactgg caaggaagac      3060
tcttatgtaa aacacagaaa acatacaaaa cgtattttta agacaaataa aaacagaact      3120
tgtacctcag atgatactgg agattgtgtt gacatattag cattatcact gtcttgctaa      3180
aacataaaaa taaaaagatg gaagatgaaa ttacaataca aatgatgatt taaacatata      3240
aaaggaaaat aaaaattgtt ctgaccaact actaaaggaa gacctactaa agatatgcca      3300
tccagcacat tgccactcta catgtggtct gtaaaccagc agcataggcg gccgcattag      3360
c                                                                     3361

<210> SEQ ID NO 29
<211> LENGTH: 143
<212> TYPE: DNA
<213> ORGANISM: Artificial Sequence
<220> FEATURE:
<223> OTHER INFORMATION: Synthetic

<400> SEQUENCE: 29
attcaacagc tgaatcctaa attgcaaact cagtggctaa taacaacttt gaacaatgag       60
caccttatac acgctactgt attttctttt ctttcttttt ttttttttttt ttttttttta      120 aaccgggtag cagtgagaga ggt                                              143

<210> SEQ ID NO 30
<211> LENGTH: 64
<212> TYPE: DNA
<213> ORGANISM: Artificial Sequence
<220> FEATURE:
<223> OTHER INFORMATION: Synthetic

<400> SEQUENCE: 30
tgtagtcatt ttgcaatcct taaagctgaa ttgtgcaatg agctcgatga aggaagatac       60
tatc                                                                   64

<210> SEQ ID NO 31
<211> LENGTH: 73
<212> TYPE: DNA
<213> ORGANISM: Artificial Sequence
<220> FEATURE:
<223> OTHER INFORMATION: Synthetic

<400> SEQUENCE: 31
ttctttaagt gccttggggc gaggagtccg gaataagaag acttctttgg gttttaaagt       60
gtaggataag caa                                                         73

<210> SEQ ID NO 32
<211> LENGTH: 1697
<212> TYPE: DNA
<213> ORGANISM: Artificial Sequence
<220> FEATURE:
<223> OTHER INFORMATION: Synthetic

<400> SEQUENCE: 32
agccctgccc ccatccgacc tccgccctcg ttggcttcgc aacgctgtgg tctctgtggc       60
cagtagaggg cacacttact ttactttcac aaatccgaga gccacaaccc gggtggtggg      120
```

-continued

```
gggtgagggg gcggggaaag agtctctgca gcaaaacgca gactagggat tggtggctct      180
tggtgtttga ggcaaaatcc tagaggctgt agtcattttg caatccttaa agctgaattg      240
tgcaatgagc tcgatgaagg aagatactat cattcaacag ctgaatccta aattgcaaac      300
tcagtggcta ataacaactt tgaacaatga gcaccttata cacgctactg tattttcttt      360
tctttctttt tttttttttt tttttttttt aaaccgggta gcagtgagag aggtttcttt      420
aagtgccttg gggcgaggag tccggaataa gaagacttct ttgggtttta aagtgtagga      480
taagcaaatc ccgagggaat atgcattata taataaatct agaaccaatg cacagagcaa      540
aagactcatg tttctggttg gttaataagc tagattatcg tgtatatata aagtgtgtat      600
gtatacgttt ggggattgta cagaatgcac agcgtagtat tcaggaaaaa ggaaactggg      660
aaattaatgt ataaattaaa atcagctttt aattagctta acacacacat acgaaggcaa      720
aaatgtaacg ttactttgat ctgatcaggg ccgacttttt tttttaagtg cataattacg      780
attccagtaa taaaagggga aagcttgggt ttgtcctggg aggaaggggt taacggtttt      840
ctttattcta gggtctctgc aggctcccca gatctgggtt ggcaattcac tcctcccct       900 ttctgggaag tccgggtttt ccccaacccc ccaattcatg gcatattctc gcgtctagcg      960
ccttgatttt ccccacccca gctcctaaac cagagtctgc tgcaaactgg ctccacaggg     1020
gcaaagagga tttgcctctt gtgaaaaccg actgtggccc tggaactgtg tggaggtgta     1080
tggggtgtag accggcagag actcctcccg gaggagccgg gtagagcgca cccgccgcca     1140
ctttactgga ctgcgcaggg agacctacag gggaaagagc cgcctccaca ccacccgccg     1200
ggtggaagtc cgaaccggag gtgctggagt gtgtgtgtgg gggggggggg gaatctgcct     1260
tttggcagca aattggggggg ggggtcgtt ctggaaagaa tgtgcccagt caacataact     1320
gtacgaccaa aggcaaaata cacaatgcct tccccgcgag atggagtggc tgtttatccc     1380
taagtggctc tccaagtata cgtggcagtg agttgctgag caattttaat aaaattccag     1440
acatcgtttt tcctgcatag acctcatctg cggttgatca ccctctatca ctccacacac     1500
tgagcggggg ctcctagata actcattcgt tcgtccttcc ccctttctaa attctgtttt     1560
ccccagcctt agagagacgc ctggccgccc gggacgtgcg tgacgcggtc cagggtacat     1620
ggcgtattgt gtggagcgag gcagctgttc cacctgcggt gactgatata cgcagggcaa     1680
gaacacagtt cagccga                                                    1697
```

```
<210> SEQ ID NO 33
<211> LENGTH: 146
<212> TYPE: DNA
<213> ORGANISM: Artificial Sequence
<220> FEATURE:
<223> OTHER INFORMATION: Synthetic

<400> SEQUENCE: 33
tcacagacac tacagaatgt tttggagatt atgtaatatt taaaatattc aaattatact       60
aaaaatgtat gtaaaatgta ttgaacatag gcaagtttca atacatagat tttgagtgaa      120
tgcttgcaac tttggttcca ttctct                                           146
```

```
<210> SEQ ID NO 34
<211> LENGTH: 77
<212> TYPE: DNA
<213> ORGANISM: Artificial Sequence
<220> FEATURE:
<223> OTHER INFORMATION: Synthetic
```

<400> SEQUENCE: 34
tctgactctg cactctgcaa cctactctaa tattacatat gataacatga gtctatgcag    60
ctgttctcta tagatat                                                   77

<210> SEQ ID NO 35
<211> LENGTH: 110
<212> TYPE: DNA
<213> ORGANISM: Artificial Sequence
<220> FEATURE:
<223> OTHER INFORMATION: Synthetic

<400> SEQUENCE: 35
ctacttcctt aaggtggtgt ccaagagtac atttttataa ataaaaagtt atagtacact    60
cctaagggca gcaagtagaa aacgtgctag ggagactcga tctcactttg               110

<210> SEQ ID NO 36
<211> LENGTH: 2195
<212> TYPE: DNA
<213> ORGANISM: Artificial Sequence
<220> FEATURE:
<223> OTHER INFORMATION: Synthetic

<400> SEQUENCE: 36
aagcttcctt ggaattaatg gtcagataag gagctctagc aatatcactt taaatgctta    60
atatacaata tttagaaaac cttatgattg taaagagctt aaaaaagatg tgaaagaaca    120
atcactaaag cattgacaac atatgtgtgt tagtgaacaa tatgtaccaa aatggacaga    180
tgagaggtgt acattggggt gtgagttgat aatccagcag actgtgggac tagagggtct    240
acgaaaaaca aaggaagaac atacaaacaa attttaaaac actgtctttc aacactaaaa    300
ctgttggaat agagagcaag aatacatatt ggattcacat tcagtttatt tctcagattc    360
agactagtgc tctgactctg cactctgcaa cctactctaa tattacatat gataacatga    420
gtctatgcag ctgttctcta tagatattca cagacactac agaatgtttt ggagattatg    480
taatatttaa aatattcaaa ttatactaaa aatgtatgta aaatgtattg aacataggca    540
agtttcaata catagatttt gagtgaatgc ttgcaacttt ggttccattc tctctacttc    600
cttaaggtgg tgtccaagag tacatttttta taaataaaaa gttatagtac actcctaagg    660
gcagcaagta aaaacgtgc tagggagact cgatctcact ttggaatcta tcctgggaga    720
caaatgcctc tacaaatgga ttagagaaga cagtttttaaa gaggaagata atcaggtaaa    780 atctgggggtt ttatgagaga aagaaagagg tagaagaaaa aatttcaagc tcgaacatcg    840
gatcaggtgg cacaatgcgg tcaatgcctg caaactcagg gtaagtatta ttctccctgt    900
ttacagttcc gtggaggaga agtgacttgc ctgtggtcat acaacagagc aaagaaaagg    960
cttgagctag aactcaggcc tttgttaggt ctccccttcc tcctagcaca ttggcaaatt    1020
gcatgaggaa agtagaggta cagttgagtt catgtacaac aataaggcat tcaggtaaag    1080
tgaatgaggg cagaagtttt atgatttagg gaaggtgtaa gacaggaaaa tatctttgtt    1140
cccaattaag aaagagatcc cttgaccatc agttagagat tcccccaagt ccctctttgc    1200
cataagtcac tgaaactgag atccaaggca tggcttctgt gagtcaggag agcttaaccc    1260
agaggagaga tttcagaaca ggatatttcc tattttgagt atcctgctca tgccagtcat    1320
ggataaattt gcatctggct taagaaatta ctggatcagc attgttttgg gtagtttcac    1380
ttcctgctgg gtggggtagc aggctctata aagagatcct ctgctgcacg actcttaaac    1440
ccctggtacc tgagcactga tctgccttgg agaacctggt gagtcggctt ccttgagttc    1500

-continued

```
ctctgttctt tgtgccctga aatgttgagt ttaatctgaa tatggcaagt ttggtggatc    1560
caatcctatg aaaattgact tgatgctact tagtggatga aaatttaaga ttagagcaca    1620
attatatgct attttagctt tcttttgtta tacaggtagg tatccatatg gacagagaag    1680
ttaaggggta acctttgata tgaagaagaa aaaagaacaa agtatttttc tttattctct    1740
tgctttctag tgtcctttac aaaggtttgt gtcttagcag gtgtgaaaga ctacaattct    1800
ccctgagcag ccctttgctc tatgcccaag tcagcccact tggactttat aacagataat    1860
gatgatagga atagcatatt agattgccca gggtgtctga acttgtgact gcctttcttg    1920
aattggttat tttcagggaa ataagatgct tgattcttta taacagagat aatttatttg    1980
gaaaaattgt atgagaaaac acaggatttc ctagggacaa tgaagcaatt tgttaaagtg    2040
gaagggagaa accagaaagt cttgaaaagg taattaagaa tttaaataat ttcttggaga    2100
ttggagaaat aatatgccat ggtattacac aagctttggc ttctctctct ggaggattcc    2160
cttcccacga acactgttgt atcatttctt tcaga                               2195
```

MATRIX ATTACHMENT REGIONS AND USES IN PROMOTING GENE EXPRESSION

CROSS REFERENCE TO RELATED APPLICATIONS

This application is a U.S. National Stage Application under 35 U.S.C. 371 of International Application No. PCT/US2019/64910, filed Dec. 6, 2019, which claims the benefit under 35 U.S.C. § 119(e) of U.S. Provisional Application Ser. No. 62/776,643 filed Dec. 7, 2018, the content of which is incorporated by reference in its entirety into the present disclosure.

SEQUENCE LISTING

The instant application contains a Sequence Listing which has been submitted electronically in ASCII format and is hereby incorporated by reference in its entirety. Said ASCII copy, created on Jun. 4, 2021, is named 45AH288805USSL.txt and is 56.0 kb in size.

BACKGROUND

Transcription of gene sequences (i.e., production of mRNA) is controlled at a number of different levels. Transcription initiation sites, or promoters, have different strengths, and the frequency of initiation of transcription of a given gene can also be augmented by enhancer sequences. Pausing during transcription can influence the rate of transcription and, hence, the amount of transcript produced in a given time period. Rates of pre-mRNA splicing, polyadenylation and cleavage can also influence the level of mRNA produced by a transcription unit. In addition, sequences within a mRNA molecule can regulate its transport from the nucleus to the cytoplasm, and its rate of turnover (i.e., its cytoplasmic stability).

Expression of polypeptides (e.g., therapeutic antibodies, growth factors) in vitro is important for the pharmaceutical industry, and methods to maximize protein expression are needed.

SUMMARY

The present disclosure describes a new technology for evaluating the strength of matrix attachment regions (MAR) and shows that the technology is useful for identifying new MAR sequences that were previously unknown. Chimeric MAR sequences are also described.

The present disclosure also describes nucleotide constructs that include cis MAR placements and related other sequences for optimal expression of genes of interest (GOI).

In accordance with one embodiment of the present disclosure, therefore, provided is a recombinant polynucleotide comprising a coding sequence, a promoter configured to initiate the transcription of the coding sequence, and a matrix attachment region (MAR) core selected from the group consisting of SEQ ID NO: 1, 5, 9 and 13, and nucleic acid sequences having at least 75% sequence identity to any one of SEQ ID NO: 1, 5, 9 and 13, wherein the MAR core is capable to attach to a mammalian nuclear matrix.

Another embodiment provides a method of transfecting to a cell a coding sequence, comprising contacting the cell with a first polynucleotide comprising the coding sequence and a promoter for initiating transcription of the coding sequence, and a second, unlinked polynucleotide comprising a matrix attachment region (MAR) core selected from SEQ ID NO:

1, 5, 9 and 13, and nucleic acid sequences having at least 75% sequence identity to any one of SEQ ID NO: 1, 5, 9 and 13, wherein the MAR core is capable to attach to a mammalian nuclear matrix, under conditions for the first and second polynucleotides to transfect into the cell.

Chimeric matrix attachment regions (MAR) are also provided, comprising (a) a MAR core selected from SEQ ID NO: 1, 5, 9 and 13, and nucleic acid sequences having at least 75% sequence identity to any one of SEQ ID NO: 1, 5, 9 and 13, wherein the MAR core is capable to attach to a mammalian nuclear matrix, (b) a 5' flanking region selected from SEQ ID NO: 2, 6, 10, 14, 18, 22, 26, 30 and 34 and nucleic acid sequences having at least 75% sequence identity to any one of SEQ ID NO: 2, 6, 10, 14, 18, 22, 26, 30 and 34, and (c) a 3' flanking region selected from SEQ ID NO: 3, 7, 11, 15, 19, 23, 27, 31 and 35 and nucleic acid sequences having at least 75% sequence identity to any one of SEQ ID NO: 3, 7, 11, 15, 19, 23, 27, 31 and 35, wherein the MAR core, the 5' flanking region and the 3' flanking region are not from the same natural MAR.

DETAILED DESCRIPTION

I. Definitions

Figure 1:
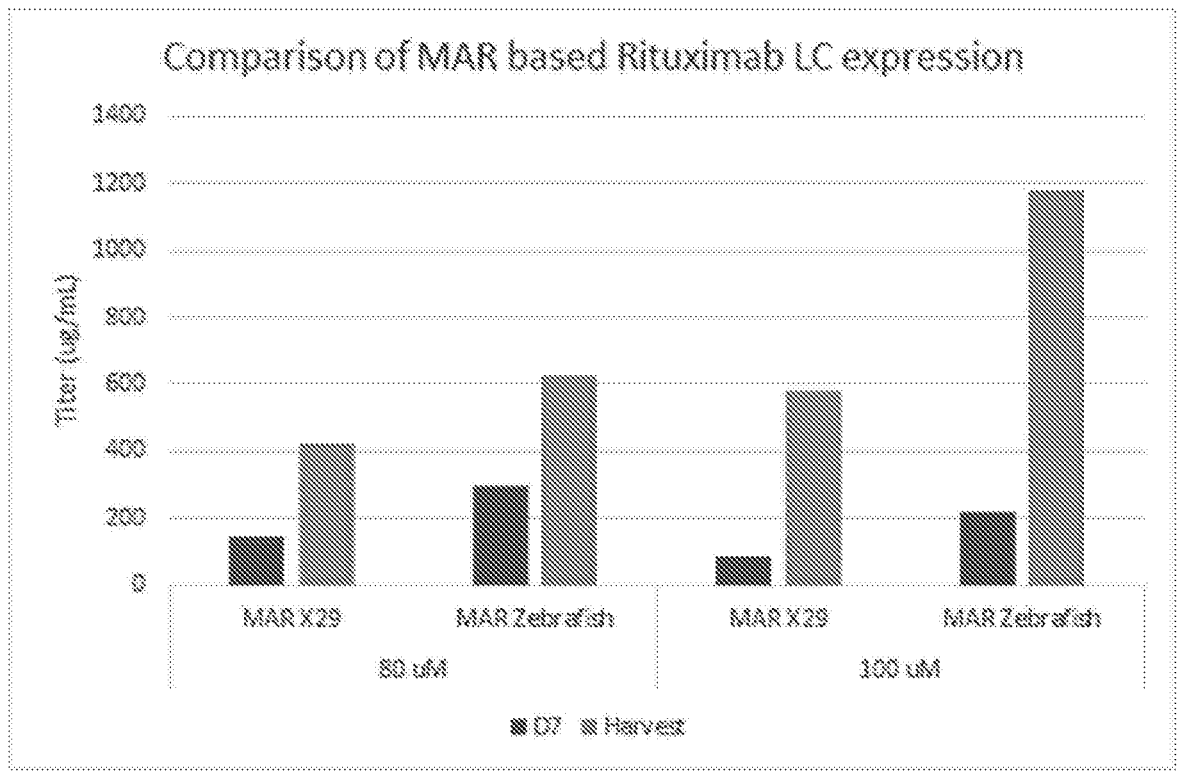
FIG. 1 compares the strength of two MAR sequences, MAR X29 a known MAR as control, and MAR Zebrafish, which was identified by the present technology.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are known in the art.

As used in the specification and claims, the singular form "a", "an" and "the" include plural references unless the context clearly dictates otherwise. For example, the term "a polynucleotide" includes a plurality of polynucleotides, including mixtures thereof.

The terms "polynucleotide" and "oligonucleotide" are used interchangeably and refer to a polymeric form of nucleotides of any length, either deoxyribonucleotides or ribonucleotides or analogs thereof. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this disclosure that is a polynucleotide encompasses both the double-stranded form and each of two complementary single-stranded forms known or predicted to make up the double-stranded form.

II. New Matrix Attachment Region (MAR) Sequences

The present disclosure describes a method to quantify the strength of a MAR element in silico and used this method to quantify the strength of new MAR sequences identified from sequence databases.

Through sequence comparison and structure-activity analyses, the instant inventors discovered that a MAR element is likely comprised of a central AT-rich core region, along with 5' and 3' flanking regions containing transcription factor binding motifs.

The core region may be enriched in the (ATAT)n microsatellite. The binding motifs may target the SATB1, NMP4, CEBP, Fast and Hox transcription factors. Additional nuclear matrix proteins that the MAR may bind to include the ARBP protein (attachment region binding protein), which recognizes the consensus sequence ATTTCA$^{C}/_{G}$TTGTAAAA in the MAR, the NMP-2 protein, localized exclusively in the nuclear matrix, the Spl, ATF, CCAAT, C/EBP, and AP-1 transcription factors, the yeast ACBP protein (ARS consensus binding protein), which interacts with the ARS element, the tissue-specific human SATB1 protein, expressed predominantly in thymus that binds to the minor groove of a special class of AT-rich MARs with A, T, or C but not G on one strand, the matrin 3 protein, an acidic protein of the internal nuclear matrix network of human and rat cells, matrin F/G, the transcription protein factor RFP.

The analytical results assisted the inventors in the search for new MAR sequences, leading to discovery of four new MAR sequences that are highly effective in promoting gene expression, as compared to a positive reference, MAR X29 (Arope et al. (2013) PLoS ONE 8(11): e79262).

It is further demonstrated that the cores of these newly identified MAR sequences can form functional MAR with the 5' and 3' flanking regions from other MARs, providing additional useful chimeric MAR sequences.

In accordance with one embodiment of the present disclosure, therefore, provided is a recombinant polynucleotide comprising a coding sequence, a promoter configured to initiate the transcription of the coding sequence, and a matrix attachment region (MAR) core described herein and variants thereof. Examples of such new MAR cores are listed in Table 1. See, e.g., SEQ ID NO: 1, 5, 9 and 13.

Matrix attachment regions, or MARs, are sequences in the DNA of eukaryotic chromosomes where the nuclear matrix attaches. As architectural DNA components that organize the genome of eukaryotes into functional units within the cell nucleus, MARs can mediate structural organization of the chromatin within the nucleus. These elements constitute anchor points of the DNA for the chromatin scaffold and serve to organize the chromatin into structural domains. The dynamic and complex organization of the chromatin mediated by MAR elements plays an important role in the regulation of gene expression.

Variants of the MAR cores are nuclei acid sequences that have certain sequence identity (e.g., at least 75%, 80%, 85%, 90%, 95%, 97%, 98%, or 99%) to the reference MAR core (e.g., SEQ ID NO: 1, 5, 9 and 13) and have the expected MAR function (e.g., capability to attach to a mammalian nuclear matrix).

In some embodiments, the variants of the MAR cores are AT-rich, e.g., having at least 75%, 80%, 85%, 90%, or 95% A or T in the sequence.

The MAR core can be present along with a 5' flanking region of a MAR, such as any one of SEQ ID NO: 2, 6, 10, 14 and 18 or their variants (an nucleic acid sequence having at least 75%, 80%, 85%, 90%, 95%, 97%, 98%, or 99% sequence identity to any one of SEQ ID NO: 2, 6, 10, 14 and 18). In some embodiments, the 5' flanking region is 5' to, and within 100 nucleotides from, the MAR core.

In some embodiments, the MAR core can be present further along with a 3' flanking region of a MAR, such as any one of SEQ ID NO: 3, 7, 11, 15 and 19 or their variants (an nucleic acid sequence having at least 75%, 80%, 85%, 90%, 95%, 97%, 98%, or 99% sequence identity to any one of SEQ ID NO: 3, 7, 11, 15 and 19). In some embodiments, the 3' flanking region is 3' to, and within 100 nucleotides from, the MAR core.

Non-limiting MAR sequences that include a MAR core, a 5' flanking region and a 3' flanking region include SEQ ID NO: 4, 8, 12 and 16, and nucleic acid sequences having at least 75%, 80%, 85%, 90%, 95%, 97%, 98%, or 99% sequence identity to any one of SEQ ID NO: 4, 8, 12 and 16, wherein the MAR is capable to attach to a mammalian nuclear matrix.

III. Chimeric MAR Sequences

As provided, the cores of these newly identified MAR sequences can form functional MAR with the 5' and 3' flanking regions from other MARs, providing additional useful chimeric MAR sequences.

In one embodiment, a chimeric MAR of the present disclosure includes a MAR core as disclosed herein with a 5' flanking region on the 5' side. In one embodiment, a chimeric MAR of the present disclosure includes a MAR core as disclosed herein with a 3' flanking region on the 3' side. In one embodiment, a chimeric MAR of the present disclosure includes a MAR core as disclosed herein with a 5' flanking region on the 5' side and a 3' flanking region on the 3' side.

The 5' flanking region can be selected from any 5' flanking region or 3' flanking region known in the art or disclosed herein. In some embodiments, the 5' flanking region can be selected from any 5' flanking region known in the art or disclosed herein.

The 3' flanking region can be selected from any 5' flanking region or 3' flanking region known in the art or disclosed herein. In some embodiments, the 5' flanking region can be selected from any 3' flanking region known in the art or disclosed herein.

Each of the MAR core, MAR 5' flanking region and MAR 3' flanking region can be substituted with a nucleic acid variant (e.g., having at least 75%, 80%, 85%, 90%, 95%, 97%, 98%, or 99% sequence identity to the reference sequence) as well.

The MAR cores disclosed herein include SEQ ID NO: 1, 5, 9 and 13. The 5' flanking regions disclosed herein include SEQ ID NO: 2, 6, 10, 14, 18, 22, 26, 30 and 34. The 3' flanking regions disclosed herein include SEQ ID NO: 3, 7, 11, 15, 19, 23, 27, 31 and 35.

The MAR flanking sequences newly identified here can also be fused to the other core sequences, either newly discovered here or known, to generate new chimeric MAR sequences, in some embodiment. In some embodiments, a chimeric MAR sequence includes any one of the MAR core regions of Table 1, any one of the MAR 5' flanking sequences of Table 1, and any one of the MAR 3' flanking sequences of Table 1.

IV. Gene Expression

The MAR sequences and constructs disclosed herein can be useful for promoting gene expression in cells. When a gene of interest is included in a construct that contains the MAR (MAR alone or with 5' and/or 3' flanking regions), the construct can be introduced into a host cell for expressing the gene of interest.

The MAR sequences disclosed herein can also be used in trans to promote gene expression, as a trans-acting element. For instance, a construct that includes any of the MAR sequences disclosed herein (MAR alone or with 5' and/or 3' flanking regions, wild-type or chimeric) can be introduced into a cell that is further transfected (or has been transfected) with a construct containing a gene of interest (GOI, or transgene) such that the MAR sequence can assist the expression of the GOI.

In accordance with one embodiment of the present disclosure, therefore, provided is a method of transfecting to a cell a coding sequence, comprising contacting the cell with a first polynucleotide comprising the coding sequence and a promoter for initiating transcription of the coding sequence, and a second, unlinked polynucleotide comprising a matrix attachment region (MAR) core as disclosed herein, under conditions for the first and second polynucleotides to transfect into the cell. In some embodiments, the MAR core is selected from SEQ ID NO: 1, 5, 9 and 13, and nucleic acid sequences having at least 75% sequence identity to any one of SEQ ID NO: 1, 5, 9 and 13, wherein the MAR core is capable to attach to a mammalian nuclear matrix, In some embodiments, the second polynucleotide further comprises a 5' flanking region selected from SEQ ID NO: 2, 6, 10, 14 and 18 and nucleic acid sequences having at least 75% sequence identity to any one of SEQ ID NO: 2, 6, 10, 14 and 18. In some embodiments, the 5' flanking region is 5' to, and within 100 nucleotides from, the MAR core.

In some embodiments, the second polynucleotide further comprises a 3' flanking region selected from SEQ ID NO: 3, 7, 11, 15 and 19 and nucleic acid sequences having at least 75% sequence identity to any one of SEQ ID NO: 3, 7, 11, 15 and 19. In some embodiments, the 3' flanking region is 3' to, and within 100 nucleotides from, the MAR core.

In some embodiments, the entire MAR sequence is selected from SEQ ID NO: 4, 8, 12 and 16, and nucleic acid sequences having at least 75% sequence identity to any one of SEQ ID NO: 4, 8, 12 and 16, wherein the MAR is capable to attach to a mammalian nuclear matrix.

Also provided are transfected cell prepared by the methods disclosed herein.

In any of the constructs or vectors disclosed herein, additional transcriptional regulatory sequences and/or post-transcriptional regulatory sequences can be included. Transcriptional regulatory sequences can include, for example, promoters, enhancers and polyadenylation signals. Post-transcriptional regulatory sequences include, for example, introns and PREs.

In certain embodiments, a multiple cloning site (MCS), also known as a "polylinker," is present in the vector to facilitate insertion of heterologous sequences. For example, a MCS can be disposed between a promoter and a polyadenylation signal, to facilitate insertion of transgene sequences. In vectors containing transgene sequences, the portion of the vector containing a promoter, transgene sequences a polyadenylation signal is denoted the "expression cassette."

Promoters active in eukaryotic cells are known in the art. Exemplary eukaryotic promoters include, for example SV40 early promoter, SV40 late promoter, cytomegalovirus (CMV) promoter, cytomegalovirus major immediate early (CMV-MIE) promoter, EF1-alpha (translation elongation factor-1 a subunit) promoter, Ubc (ubiquitin C) promoter, PGK (phosphogly cerate kinase) promoter, actin promoter and others. See also Boshart et al., GenBank Accession No. K03104; Uetsuki et al. (1989) *J. Biol. Chem.* 264:5791-5798; Schorpp et al. (1996) *Nucleic Acids Res.* 24:1787-1788; Hamaguchi et al. (2000) *J. Virology* 74:10778-10784; Dreos et al. (2013) *Nucleic Acids Res.* 41 (D1):D157-D164 and the eukaryotic promoter database, accessed on Jul. 16, 2014.

Enhancers can also be included on the vector. Non-limiting examples include those in CMV promoter and intron A sequences. Five embryonic stem cell (ESC) transcription factors were previously shown to occupy super-enhancers (Oct4, Sox2, Nanog, Klf4, and Esrrb), and there are many additional transcription factors that contribute to the control of ESCs. Six additional transcription factors (Nr5a2, Prdm14, Tcfcp2l1, Smad3, Stat3, and Tcf3) occupy both typical enhancers and super-enhancers and that all of these are enriched in super-enhancers. Any of these or further known in the art can be used herein.

Polyadenylation signals that are active in eukaryotic cells are known in the art and include, but are not limited to, the SV40 polyadenylation signal, the bovine growth hormone (BGH) polyadenylation signal and the herpes simplex virus thymidine kinase gene polyadenylation signal. The polyadenylation signal directs 3' end cleavage of pre-mRNA, polyadenylation of the pre-mRNA at the cleavage site and termination of transcription downstream of the polyadenylation signal. A core sequence AAUAAA is generally present in the polyadenylation signal. See also Cole et al. (1985) Mol. Cell. Biol. 5:2104-2113.

Exemplary introns that can be used in the vectors disclosed herein include the β-globin intron and the first intron of the human/mouse/rat/other species cytomegalovirus major immediate early (MIE) gene, also known as "intron A."

Additional post-transcriptional regulatory elements that can be included in the vectors of the present disclosure include, without limitation, the 5'-untranslated region of CMV MIE, the human Hsp70 gene, the SP163 sequence from the vascular endothelial growth factor (VEGF) gene, and the tripartite leader sequence associated with adenovirus late mRNAs. See, for example, Mariati et al. (2010) *Protein Expression and Purification* 69:9-15.

In certain embodiments, the vectors disclosed herein contain nucleotide sequences encoding a selection marker that functions in eukaryotic cells (i.e., a eukaryotic selection marker), such that when appropriate selection is applied, cells that do not contain the selection marker die or grow appreciably more slowly that do cells that contain the selection marker. An exemplary selection marker that functions in eukaryotic cells is the glutamine synthetase (GS) gene; selection is applied by culturing cells in medium lacking glutamine or selection with L-Methioniene Sulfoximine or both. Another exemplary selection marker that functions in eukaryotic cells is the gene encoding resistance to neomycin (neo); selection is applied by culturing cells in medium containing neomycin, Geneticine or G418. Additional selection markers include dihydrofolate reductase (DHFR, imparts resistance to methotrexate), puromycin-N-acetyl transferase (provides resistance to puromycin) and hygromycin kinase (provides resistance to hygromycin B). Yet additional selection markers that function in eukaryotic cells are known in the art.

The sequences encoding the selection marker(s) described above are operatively linked to a promoter and a polyadenylation signal. As stated above, promoters and polyadenylation signals that function in eukaryotic cells are known in the art.

In certain embodiments, a vector as disclosed herein can contain two or more expression cassettes. For example, a vector containing two expression cassettes, one of which encodes an antibody heavy chain, and the other of which encodes an antibody light chain can be used for production of functional antibody molecules.

The vectors disclosed herein also contain a replication origin that functions in prokaryotic cells (i.e., a prokaryotic replication origin). Replication origins that functions in prokaryotic cells are known in the art and include, but are not limited to, the oriC origin of *E. coli*; plasmid origins such as, for example, the pSC101 origin, the pBR322 origin (rep) and the pUC origin; and viral (i.e., bacteriophage) replication origins. Methods for identifying procaryotic replication origins are provided, for example, in Sernova & Gelfand (2008) *Brief Bioinformatics* 9(5):376-391.

The vectors disclosed herein also contain a selection marker that functions in prokaryotic cells (i.e., a prokaryotic selection marker). Selection markers that function in pro-karyotic cells are known in the art and include, for example, sequences that encode polypeptides conferring resistance to any one of ampicillin, kanamycin, chloramphenicol, or tetracycline. An example of a polypeptide conferring resistance to ampicillin (and other beta-lactam antibiotics) is the beta-lactamase (bla) enzyme. Kanamycin resistance can result from activity of the neomycin phosphotransferase gene; and chloramphenicol resistance is mediated by chloramphenicol acetyl transferase.

Exemplary transgenes include any recombinant protein or e.g., hormones (such as, for example, growth hormone) erythropoietin, antibodies, polyclonal, monoclonal antibodies (e.g., rituximab), antibody conjugates, fusion proteins (e.g., IgG-fusion proteins), interleukins, CD proteins, MEW proteins, enzymes and clotting factors. Antibody heavy chains and antibody light chains can be expressed from separate vectors, or from the same vector containing two expression cassettes.

The present disclosure provides methods for expressing a recombinant polypeptide in a cell. The methods comprise introducing a vector as described herein into a cell and culturing the cell under conditions in which the vector is either transiently or stably maintained in the cell. Cells can be prokaryotic or eukaryotic, such as stable cell lines generated by targeted integration with CRISP/Cas9. Cultured eukaryotic cells, that can be used for expression of recombinant polypeptides, are known in the art. Such cells include fungal cells (e.g., yeast), insect cells, plant cells and mammalian cells. Accordingly, the present disclosure provides a cell comprising a vector as described herein.

Exemplary yeast cells include, but are not limited to, *Trichoderma* sp., *Pichia pastoris, Schizosaccharomyces pombae* and *Saccharomyces cerevisiae*. Exemplary insect cell lines include, but are not limited to, Sf9, Sf21, and *Drosophila* S2 cells. Exemplary plant cells include, but are not limited to, *Arabidopsis* cells and tobacco BY2 cells.

Cultured mammalian cell lines, useful for expression of recombinant polypeptides, include Chinese hamster ovary (CHO) cells, human embryonic kidney (HEK) cells, virally transformed HEK cells (e.g., HEK293 cells), NSO cells, SP20 cells, CV-1 cells, baby hamster kidney (BHK) cells, 3T3 cells, Jurkat cells, HeLa cells, COS cells, PERC.6 cells, CAP® cells and CAP-T® cells (the latter two cell lines being commercially available from Cevec Pharmaceuticals, Cologne, Germany). A number of derivatives of CHO cells are also available such as, for example, CHO-DXB11, CHO-DG-44, CHO-K1, CHO-S, or engineered CHO cells such as CHO-M, CK1 SV CHO, and CHOZN. Mammalian primary cells can also be used.

In certain embodiments, the cells are cultured in a serum-free medium. For example, for manufacture of therapeutic proteins for administration to patients, expressing cells must be grown in serum-free medium. In additional embodiments, the cells have been pre-adapted for growth in serum-free medium prior to being used for polypeptide expression.

The vectors as described herein can be introduced into any of the aforementioned cells using methods that are known in the art. Such methods include, but are not limited to, polyethylene glycol (PEG)-mediated methods, electroporation, biolistic delivery (i.e., particle bombardment), protoplast fusion, DEAE-dextran-mediated methods, and calcium phosphate co-precipitation. See also, Sambrook et al. "Molecular Cloning: A Laboratory Manual," Third Edition, Cold Spring Harbor Laboratory Press, 2001; and Ausubel et al., "Current Protocols in Molecular Biology," John Wiley & Sons, New York, 1987 and periodic updates.

Standard methods for cell culture are known in the art. See, for example, R. I. Freshney "Culture of Animal Cells: A Manual of Basic Technique," Fifth Edition, Wiley, New York, 2005.

EXAMPLES

The disclosure is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications fall within the scope of the appended claims.

Example 1. Search for New MAR

This example developed a method to quantify the strength of a matrix attachment region (MAR) element in silico and used this method to quantify the strength of a few exemplary MAR sequences.

Motif-Based MAR Identification

A literature search was performed to identify all motifs related to MAR identification, specifically looking for MAR specific transcription factors, chromatin binding domains, DNA bending and DNA unwinding sequences. Potentially useful characteristics were summarized and used for further MAR evaluation.

A MAR element is likely comprised of a central AT-rich core region and the 5' and 3' flanking regions containing transcription factor binding motifs. The core region may be enriched in the (ATAT)n microsatellite.

A MAR may contain and be generally categorized by the inclusion of a "MAR recognition signature," a bipartite element composed of two distinct sequences AATAAYAA and AWWRTAANNWWGNNNC. Other MAR indicative sequences consist of various transcription factors and DNA structure motifs. Exemplary sequences include the DNA-unwinding motif, AP-1, A-box and T-box, NMP-2, SATB1, Hox4D, TEF, Pit1 and Fast.

Four new MAR elements were identified through the search, named as MAR Zebrafish, MAR *Cyprinus Carpio*, MAR 12-RP13, and MAR 17XX_fos, respectively. Their, as well as a few known ones' (MAR 1-68, MAR S4, MAR X29, Mouse c-myc SMAR, and SPR2A-MAR), completed sequences, core and 5' and 3' flanking regions of the core are listed in Table 1.

TABLE 1

MAR Sequences

| Name (SEQ ID NO:) | Sequence |
|---|---|
| MAR Zebrafish core (SEQ ID NO: 1) | AAATAATTAATTAGCAAATAATTTATATATTTATATATTTATATATATAT ATATATATATATATATATATATATATATATATATATATATATATATATAT ATATATATATATATATATATATATATATATATATATATATATATATATAT AAATATATAAATATATATATATATATATATTGGT |
| MAR Zebrafish core 5' flanking region (SEQ ID NO: 2) | AAATATTTCAAAAATTAAGCAAAGAAACTTTCACAGTATGACTAATAATA TTTTTTCTTCTGGAGAAAGTCTTATTTGTCTTATTTCGGCTAGAATAAAA ACAGTTTTTAATTTTTTAAACACCATTTTACGGACAAAATTATTAGCCCC TTTAAGCTATATTTATTTTCAATAGTCTACAGAAC |
| MAR Zebrafish core 3' flanking region (SEQ ID NO: 3) | GGGAGAAGCAGTCCAATGTGGCTGTATATATATATTATTATTTTTTTTTT TTTAAATACAAACAATTAAGCTGTCGAACTGTTGTATAAACACAATAT |
| MAR Zebrafish (SEQ ID NO: 4) | ATGCAAAGGACTCTTTCTGTAAAATATCTGCTGTAAAAATCTAAAGGATT TGAGGGTTGCACTCCCAAAGGCTCCTGAGAGCTTGTGTAAAATAAGCCTT CCTAACTGCTGCTTTCTCACTTTAGTCAATTTTGGCCTTTTTTATATTCA TATACAGTAAATGTTGCTCTAATCAATGTGGATGATCATTATCAGTATAT GACTCGAAAAATATTTTAAACTTCTCTTTGCTTCTAGACCAGGATTTGAA GGAATATTCTATTTTTAATGACACTGCTTTGCAATATTTATGATTCTTAA AGTCAAACAGAGTGAAACAGAAGTAAACATGTCATGATGTACACTCACAT GAAACAATCTCTGAAATGAAGAATGAATGAAGAAAGTTGTGTTGCTAACA AAATGGAGGAAGACTCACGAATAGACAAAAGCAGGGCAGAAACGAGACAC GCACCCGTGTACATATATACAGTTGAAGTCAGACTTATTAGCCCCCCTTT GATTTTTTTTTCTTTTTTTAAATATTTCAAAAATTAAGCAAAGAAACTTT CACAGTATGACTAATAATATTTTTTCTTCTGGAGAAAGTCTTATTTGTCT TATTTCGGCTAGAATAAAAACAGTTTTTAATTTTTTAAACACCATTTTAC GGACAAAATTATTAGCCCCTTTAAGCTATATTTATTTTCAATAGTCTACA GAACAAATAATTAATTAGCAAATAATTTATATATTTATATATTTATATAT ATATATATATATATATATATATATATATATATATATATATATATATATAT ATATATATATATATATATATATATATATATATATATATATATATATATAT ATATAAATATATAAATATATATATATATATATATATTGGTGGGAGAAGCA GTCCAATGTGGCTGTATATATATATTATTATTTTTTTTTTTTTTAAATACA AACAATTAAGCTGTCGAACTGTTGTATAAACACAATATCACTCGAGTTGC AGTCCGATGTGACTATATATTGGCACTGGTGGGAGATTTGCATTCATTGT GACAATATACAGCCACATTGCATTGCTACGAGTGTGATATTATGTTTATA CACCAGTTCAACAGCATAATCGTGTGTAATAAAAAGATAATCAAACACGG AAGAGGAACTACTTTCTTCCGCCATTCATTCACATCTGCAGCTTACGTCA GAACAGCAGAAGCTGTTGCTCATTCATATATATAATATATATAAATTTGT ATACTTACAGACGACACAGTGGCTCAGTGGTTAGCACTGTCTCCTCACAG CAAGAAGGTCACTGTTTCAAGTCCAGGCTGGGTCCGCCGGCATTTGTGTG TGGAGTTTGCTTGTTTTTCCCGTGTTAATGTGTATGGATGTTTCCCAGTA CTGGGTTGCAGCTGGAAGGGCATCCGCTGTGTAAAACTTATGCTGGATAA GTTGGCAGTTCATTCGCTGTGTCAACCCCTGATGAATAAAGGGATTAAG CCAAATGAAAATGAATGAATGATTTAATACTCTTGTTTAAGTCTTAGTGC CGATTATATATAGATATGTGGTGTTAGATCAAACCAGTGTTCATTTTGAC AGCAAAATTTGATTTAGTTTTAGTCATTTTTTAGTCTTCCATATTCGTTA TAGCATCAGTCTATATACAGTCAACTAAATTAAACATGATTTTAGTCAAC TTCATGCATTTTCACATGGACAAGGTCATTAAAATTCTACAGGATCAGGT TGTACCAACTCTATCTCATGGAAATTTGTAACTTTTTGATTGTGGCTAAT TCGTATGAATTTGTATGATCTCATTTGTACAATTTAGTATTATTTGCTCA TCCCCCAGTGATGGTTGGATTTAGGGTTG |
| MAR Cyprinus Carpio core (SEQ ID NO: 5) | TATCCAAATATATATATATATATATATATATATATACTATATATATATAT ATATATATATATATATATATATATATATATATATATATATATATATATAT ATATATATATATATATATATATATATATATATATATATATATATATATAT ATATATATATATATATATATATATATATATATATATATATATATATATAT TTTTTTTTTTTTTTTAAGAAAACA |
| MAR Cyprinus Carpio core 5' flanking region (SEQ ID NO: 6) | CAAATTTGCTATACAAAAACCTAAATGTAATAAAGTTACATCCATAAAAG TGACTTTTTATTACTTTTGAAACACAACAGATTTATGCCCTGTCTATATC CAGTTC |

TABLE 1-continued

| MAR Sequences | |
|---|---|
| Name (SEQ ID NO:) | Sequence |
| MAR Cyprinus Carpio core 3' flanking region (SEQ ID NO: 7) | GTTATAATAATTTTATAATCTCTCACAATATTGCTGTTTTACTGATTTTT GAATAAATGCAGCCTTGGTGAGCATAAGAGACTTTTTCTAAAAACTTTGA AAAGTCTTA |
| MAR Cyprinus Carpio (SEQ ID NO: 8) | TGTTACATTAGGCTGAAAACACACTGTGTATGTGCATATTTTCCCTTAAA TACATAAAGAAGTAATGGGTGGCGTACCTGTATTGGTTATAGACTCCAGG GCAGTATAACATGGCTGTGAATAGACTCTGTTGTGGACATACACTCCATA ACACCAAACTGATCCCGTAGAACGATGTCACCAGGAAAAGAAGGAGCGTC AAAATGAACTGCCTGTGATTGGCTTGACCTACACAGCTGTTTATCCTGTC ATGGAAAGTCACATACATACAAGACACAAATAATAAGCAACACATTTACA GATATTTTCATTCAAACAATTTAGAACAATTATACTATTTTCTCTCTTGT CAATGTAGCTTTAATGAGAATTATGTGGCTCATGGCATGTTCATATTTAT ATTTGTGCCTGTGTGTGTGTTGAAGTAGCATGGAGACAGATTGGCCTGGT GAGAGCTCCCTTTACTGTGCTGAAAACTGTGTTCCTGTTGCCTTTGCACA TGTCTCACCAGCCTGCCTGCTCCAGTGACGTCTTTTGGGAATCAGCTTGA ACATATGTGTGTGTCTGATGGGGTAGGGAACACATGCATACAAGTGTGAA GAGATCAGAAAATGAATCAAATCATTGGCATGACCACTAATTTAAACAAT TCATTTTGGAATTGTTCAGCTACTTCTGTAGTAAGGATTTGCAATAAGCC AGATATCTTAGAAGGAAAGGCACAAATATCAACATTAAAATTAATATTTG AAATAACAGAAAATATATTCGGTTGACTGATTATCCAACAAACACAAGTG TAAAGTGATATTTTTAATGAACATCTAAAATTACAATGCAACGGTAAGTC TGTGAAGCTGAGATGATTAAAATGTGATCTTTATGAATGAAAGCAGATGG CCACAATGCTCTCTCTCCTTTTATTGTTTATAAATCATAAATCATCAATT CATATAGTAACTTTTTTAGATTTTGAATATTTATTTATGTAAAGTTTTAA ATATTATTGAATAGTAAATAATTTAATATGATAATCATTTATAAAAGTGT ATATTTGTAAATACAATTATTTTTAAAATATATAAATGATGAAAAAAATT TAAATATAAGAATAAACACTTTTATAAATAATACAAGGCAAATTTGCTAT ACAAAAACCTAAATGTAATAAAGTTACATCCATAAAAGTGACTTTTTATT ACTTTTGAAACACAACAGATTTATGCCCTGTCTATATCCAGTTCTATCCA AATATATATATATATATATATATATACTATATATATATATATATATAT ATATATATATATATATATATATATATATATATATATATATATATATATAT ATATATATATATATATATATATATATATATATATATATATATATATATAT ATATTATATATATATATATATATATATATATATATATATATATATTTTTTT TTTTTTTTTTAAGAAAACAGTTATAATAATTTTATAATCTCTCACAATAT TGCTGTTTTACTGATTTTTGAATAAATGCAGCCTTGGTGAGCATAAGAGA CTTTTTCTAAAAACTTTGAAAAGTCTTACCGACAACATATTATTGAATGG CAGTGTAAATATAGATCGTTTTGTCATTTAGAGAATATTTAATTAATGTT TAATACACTTCACACTAGGAATGAAGTGCTCGTACTCAATTTTTAAAGAA GAAGGAATGAGAAACCCACCAAACACAGTGGTGGTCCATTCGAAGGACAC ATGCCCCACAGATCCTGCAGTGCCCTGCCCTTGGTGGGCGCACCTGTCGG CACACAGGGCATAACTTCTTCTTTCCTTCGTTTTCCCCATTTGACTGACT GATTCCTTTGCAGGGGGCGGAGTCTCCAGGTATGTTTGTGCTCTGATTGG TTGTACAGATACTGTTAATTCCCTGAGCTAATGACTGGGATTTGACAAAG CCTGGTCCTTGTTTGGTGCGCACAAGGGAGATAAGGGTCAACATCATGCC TGTCGTCACAGTAACCAGCTGCAGATTACTGACGTCTCCTCTGGGAACGA TCTCAGTAAGGAAAAGATAGTACATGTAGGCAAGGGAGAAAAGTGCCAAG CTAAGGAAAAACAATGTGCGTCTTTTCCTTCTGTGAGTCACATAGTAATA CCAAAGCACCAGTCCTGGTAGGGCAGTTAGGACAACAACTCCCAACATAC AGTTAATTGCTGCTACTCGCAACAGACCAGGAATTAATACCATGGGAGGT AAGACAGAGATTTCCAATCGAAGGGGGTCCTACGGCACAACATGGCAAACC CAAACGATCAGCCATACAAGAGACGAAACGAGAGAAGATGTCTGGCTTGT CTTGCTCTCCTCTGACTAACCTATTGAGAAAGAGTGACAAATTCACCATT CATCATTTACACACTATTATGTTATCAGTTTTATGTATGGAAATGACAAG GTGCAAACGGACAAAATTATTTAATTCAACTACACTTTTTAAAGTGTAAA AATGTAAAGTGTCAAAAGTTTTATATCAATAAATGTAATGTAAAACCATCT CTGCATGCCATGATCTTAACTGGTTGACCTCTGACCTTTCACAGGCATCA TCTAGTTCTTCACAGTCACAGCAGCAGTACTCTCTTTGCTGGTCGATGTC TCCACAGCAGCACAGAGGGTCATCTGGTT |
| MAR 12-RP13 core (SEQ ID NO: 9) | ATATATATATGTTAGTGATATATATATAAAATATATATCACTCTTATTAT ATATTATATATATTATATAATATATAATATATTATATTATATAATATATT ATATATTATATAATATATATAATATATTATATATTATATAATATAATATA TTTATATATTATATAATAATAATAATAATTATATATTATATAATAATATAT AATATATTATATAATAATATATAATAATATATAATATATTATTATATAAT ATATAATAATATATAATAATATAATAATGTGATTATATTATATATAATAT GTAATATAATAATGTATATATATTATATATGCATTATATATAATGATTTT |
| MAR 12-RP13 core 5' flanking region (SEQ ID NO: 10) | AATTGCATAAGCCAATCCCTTGCAATAAATAAAATAGATCGAGATGTAGA TAGACAGAGATCCAGATCCTACTGGTTCCATTTTCCTGGCAGAACCATGA TGGATATGATATATGTCCCATAAAGAGCCTCCCAGTGGTGTCTTTTTGTT TTGTAAAGATGGTTTTAATCCACAGATTTAAGAGTG |
| MAR 12-RP13 core 3' flanking region (SEQ ID NO: 11) | CTATCAAATGTATATTTAAATCTACCTACTTGTGTTATATATTTATATAT GTGTGTGTGATATGTATAATTTTAAAATATATCTGTATAGCTACTTAATT TGTATTTCCAGCCCAATTCAGTCTAGTGACAGAAAATATAACTCATCAAG TCT |

TABLE 1-continued

| MAR Sequences | |
|---|---|
| Name (SEQ ID NO:) | Sequence |
| MAR 12-RP13 (SEQ ID NO: 12) | TACCCAGTAATTCTTAAACTACTTACTCCAGCACTTGGCCCATGGCAAAT |
| | TTCCTGGTAGCCATATGTACATATACACATGCTTTTAAATACATAAACGT |
| | ATGTACATATACTTTTAATTTACTACTAAGATTTTATACATTTTCCAGTA |
| | GTTTGTATGATGAACATGTATATACCTCCCTTTAAAGTTAAACAATAAAA |
| | AAATCTTAATTTTTCTACCTTAAAATCTCCTCTCATCACGTCATCCAATG |
| | ATAGCCGCTGTTAACATCATGTTCCTATTTACTTCTGCTTGTTTCTCTGA |
| | AGATGTACGTGAGTGGGTAAACACGATGTAATTTGACATTGCGGTTTTTA |
| | ATAGCATATCACAAATATTTTCCTGTTATAATTTCATTCACAAACATGGT |
| | TCTGATAGTTACATAATATTACACCATATGATCATTTCCTAGTTTACTTA |
| | GCTATTTCCTATGGTTGGATATTCTTGGCTTGTTTCCAATATTTTTCTAT |
| | TCTAATTCATCTCCAACAAAAGTCATCATCTGTGAATCTTTCTCTGCATC |
| | TCTAAGTATTTCCTTAGAATAAACTCCTAGAGTGAATCTGTTAGCACATT |
| | TGTTTCTCTCTTTTAATTAACAACTGGAAAATGATTATTGCAGACACATT |
| | CTCTTCAAGTGAATATTTCTTCTCGGCTGAACTTTGCTTTACTGAGTATT |
| | TTTCCCTCCCTTGGCTGCATTTTCATTCTTCTTTTGCTGTTTTGCGTTTC |
| | ACTCCCACCTACAAAATATCCAAGTTCCCTCTCCCAAAATAAAACCCCTC |
| | TTGGTTCATGGCAGAGTCAACTTTGTTCAGCTGTCTTTACCCTGCAGGTC |
| | CAAAGGTCTATTGCCCAGAGTATTTGCTGAGGGGATAAGAGGTGCCAGGT |
| | CCTCATCAGAGTAATCTTTGCATCTTCCATTTTAGATGATGAGGCTGAGG |
| | CTAAATAACTTTTTGTGACTTGAACAAAATCACGCCCGTCATTTTGGAGC |
| | AGAGATTGGACCCAGACCATCTGACTGCAGTGCACTTGGTTACTACACAA |
| | CAGCCCTGGAAGCTGCAACCTGAGGACCTCCAGCCTCACATGAATCATCT |
| | TCATCCACCAACCTTCTCCCATCTGGGTTCCCACACTCCTCCCATCACCC |
| | AGCATGGGGGGCCTCATGGTGGTGGTTGACCCTTCCTCTATCTCCACCTG |
| | CATATGGGGCACATTCTCCCCAAACCTCACTCCAGTCCAATCTCACCTCA |
| | ACCCCACTGTCTCGCTCATAGGGTTGAGGAAAGACAGAATAAACCCTGGC |
| | TGGGAAAAGTCACTTTAGTCAATGTACGGTCAGTTTTACGTGTCAGCTTG |
| | GCCAGGCTAGAGTCCCCAGTCATCCAAACGCCCAGTTGACTGTAAGCAAA |
| | GACTATCCTAGATAATTTGGTCGGCCTGAGACATTCAGTTAAAAGACCAT |
| | AAGAGCAGAACTGAAAACAGAAAATTCTGCCTGTGGACTGCAGCGCCAGC |
| | TCCTGCCTGAGAGTTTCCAGCCTGACCTTCCTAAACTTGCCTACTAATCC |
| | CCCACAATTGCATAAGCCAATCCCTTGCAATAAATAAAATAGATCGAGAT |
| | GTAGATAGACAGAGATCCAGATCCTACTGGTTCCATTTTCCTGGCAGAAC |
| | CATGATGGATATGATATATGTCCCATAAAGAGCCTCCCAGTGGTGTCTTT |
| | TTGTTTTGTAAAGATGGTTTTAATCCACAGATTTAAGAGTGATATATATA |
| | TGTTAGTGATATATATATAAAATATATATCACTCTTATTATATATTATAT |
| | ATATTATATAATATATAATATATTATATTATATAATATATTATATATTAT |
| | ATAATATATATAATATATTATATATTATATAATATAATATATTATATATT |
| | ATATAATAATATAATATATTATATATTATATAATAATATATAATATATTA |
| | TATAATAATATAATAATATATAATATATTATTATATAATATATAATAA |
| | TATATAATAATATAATAATGTGATTATATTATATATAAATATGTAATATAA |
| | TAATGTATATATATTATATATGCATTATATATAATGATTTTCTATCAAAT |
| | GTATATTTAAATCTACCTACTTGTGTTATATATTTATATATGTGTGTGTG |
| | ATATGTATAATTTTAAAATATATCTGTATAGCTACTTAATTTGTATTTCC |
| | AGCCCAATTCAGTCTAGTGACAGAAAATATAACTCATCAAGTCTGGGTAA |
| | TCTCAAATAATTCGGCTAAATTCCTCAATTCATCAATTTCTCCCTCCTCC |
| | AGCCTCCGCATAATTGATTCTAACTTTCAGGGAGTTGAAGCAGCACTGCC |
| | CTGGGGGGCTCTCTTCCAGCTCTCAGCCCCTCCCTGCACAGCTCTGGTGC |
| | CCACGGGGATGCGCCCACGGGGATGCAAGGCCCTGTATGACCATCAGACC |
| | TCCTGTCCTCACTTGAGATGTTTATTTCTAGTCCCCAGTCCTGCCCCAAC |
| | CACAGGATGTAACCCAGACCCTGGTCTCTATTCCAAGATTCATCCTTGTC |
| | AAGCGGTTCTCAGCAGCATGCCTCTGCCACGCCCAGTCACAGAGGACGAT |
| | ATTGGCTCCCCTCTTTATGGGGGGAGGATAAAAAGGATCATATCCCAGAC |
| | CCCTGGGCTTAAGGCTTCCATGTTCCCATCTCTACTCTTTAATGCCAGGA |
| | TGACATAGGGTACTTTCTGCAGGCATAGACAACCAGGCAGGAAGAGGGGC |
| | CCATGTTCCTTGTAATCTCAGATCACAAGTACCCTCTGGGGATCTATCAC |
| | CCCAAGCTTGGTGCATGGACAAGGGGTACCTTATTCTCTTCCTTTCTTCT |
| | AAGACTATGCACTGCCTCTCCCCCAGGCAAATGGAATCTTGTCAATTCCA |
| | AGTGAGTTTGGAAAAACTCATTCTTTTTTACTTATTGTTTAGATCGGAAC |
| | CTAAAATCGAAAGTTCCAGGAAGCTCAAGTTCTTATAACTAAAAAGGCTT |
| | TTCTCTCTCAAGAGCATTGGCTCTGTCTTTTCCATGTTCTACTTTGAAAC |
| | ACAAAAGCTGAGCTCGACATTGATTTAATTGCTTTTTATTTGAATGATTG |
| | CTATAAGTGACACCTTTTGGGGCAGTATGTCCTAGCTGGTTGAATTAGAG |
| | TTGGGAAACACATTGCAAGAAAGGGTAGAAAGAGGCATACTTTATTGAAT |
| | CTTTTGGAGTAACTTTTGTGCCTGTTACCACAAGCTTATTTTTGATAAGA |
| | TGCTTCCTAACTTTCCTCGCTCACCCCTACCTCATCTCAGGGCCAAGCAC |
| | GAAAGTTGTTTTATACATGCTAGGTTTGGCTGATTTCAATGTGACTTCCC |
| | CAGGGCAGAAGAGACAGTGGTTGAAGGATGAAGAATCAACCTACCCGGGG |
| | GAATCAAAGATTGATCCCAGGGAATGGAGCAGATATAATTAAATAAGTTT |
| | TTTCTTTCCCCAGTGTATCTAATATTCATTTTTGTATTTACTTGGAGCAA |
| | ATGAATTTAAATGAATTTTTAGTTAGAGTTAAATCAACTCATTAAAACAC |
| | ATTGAAGGAATTAGAAATGTAAAATCATTTCCTGCTGCAATTCATTCATC |
| | TCTAAGTCTATAACTGACTTGAATCTAGGTAAAGGTCATTGCTTAAAGGG |
| | GACAGTGGCCCTTATTCTTGCAACCTACAAACTTTTACAGTTTGCATGGA |
| | GTTTTCACATCCATGAACTCAAGCAAGACTGAATAGGCCTGTATGGTGAA |

TABLE 1-continued

| MAR Sequences | |
|---|---|
| Name (SEQ ID NO:) | Sequence |

| | CAAACAGGAGTAAATGCCTCCACTATTCAGGGGAGGAAAGTGAGCTCAAA |
|---|---|
| | AAAGTTTAATATTGTTGCCTAAGGATACTCAACCAGCAAATGGCAATATC |
| | GAGACAGGAGCAGGTCTTCAGTCCAAACCCACAGAGCAGAGCTTGCCCAG |
| | GAAGCTGATCATTCTTGTACCACCTTCTCCATCACTGGACCTACACCCTG |
| | CCCTTCTTTACCCAGCTCTGACCTCTCAGATGCTGAACCTGGGGTGCCCT |
| | TGTCATTGAACTTCGAGTTGCATTATTTTCCCATTGTTTTACCTACAATT |
| | AACTTGCCGTC |

| MAR 17XX_fos core (SEQ ID NO: 13) | AGACTCTGTCTCAAATATATATATATTTATATATATATATTTTATATTTA |
|---|---|
| | ATATATATAATATATATTATATATAAATTTATTATATATAATATATATTA |
| | TATATAAATTTATTATATATAATATATTATATATATTATATGTTATAT |
| | ATATTTATTACATATAATATATAATATATATTTATTATATATAATATATA |
| | TTTATTATATATTATATATATTTTATATTTTATATATATTATATA |
| | ATTTTATATTTTATATATATTATATAATTAATATTTAATATATATTATAT |
| | ATATATATAATATATATTTATTATATATAATATATATTTATTATATAT |
| | TATATATTATATATTTATATTTTATATATATTATATATTTATATTTTATA |
| | TATATTATATATTTATATTTTATATATATTATATATAATATATATATTAT |
| | ATATTTATATATAATATATATTTATTATACATATTTTATATTATATATA |
| | ATATATATTTATTATATATTTTTATATATATTATATAATATATATATA |
| | TTTATATATATATTTTATATTTAATATATATAATATATATATTATATATA |
| | AATTTATTATATATAATATATATTATATATAAATTTATTATATAATAAT |
| | ATATTATATATATTATATGTTATATATATTTATTACATATAATATATAAT |
| | ATATATTTATTATATATAATATATATTTATTATATATTATATATTATATA |
| | TTTATATTTTATATATATTATATATTTATATTTTATATATATTATATATT |
| | TATATTTTATATATATTATATATAATATATATTATATCTTTTATATAT |
| | AATATATATTTATTATACATATTTTATATTATATATAATATATATATTAT |
| | ATATATATATATATATATTTATATATATATATATTTATATATTTTATA |
| | TATATAATATATATTAATTATATATAATATATATATTATATATATATT |
| | ATATATAATACGTAATATATATTTATTATATATATTTTGTATATATTATA |
| | TATTATATATTTATTATATATATTTTATATATATTATGTATATTTTATAT |
| | ACAATACATAATATATATTTTATATACAATATATAATATATATTTTATAT |
| | ACAATATATAATATATATTTTATATAATATATTTTTATATAATATATATT |
| | TTATATTATATATAATATATATTTTATATATTATATATAATATATATTTT |
| | ATATTATATAATATATATTTTTATACTATATATAATATATATTTTTATAC |
| | ATTATATAATATATATTTTATACTATATATAATATATATTTTTATACATTA |
| | TATAATATATATTTTATATATTATATAATATATATTTTATGTTATATAAT |
| | ATATATTTTATGTATTATATAACATATATTTTATGTATTATATAACGTAT |
| | ATTTTATATATTATGTAACGTATATTTTATATATTATGTAACGTATATTT |
| | TATATATTATGTAACGTATATTTTATATATTATGTAATATATATTTTATA |
| | TATTATATATTTTGTATATTATATATTTTGTATATGATATATTATATATT |
| | TTATATATTATATATTATATATTTTGTATATTATATATTATATATTTTAT |
| | ATATAATATCATATATATTTTATATATATATAAAGCATCAGTAAACAA |

| MAR 17XX_fos core 5' flanking region (SEQ ID NO: 14) | TAACATGGTGAAATATCATCTCTACTAAAAATACAAAAAATTAGCCAGGC |
|---|---|
| | GTGGTGGCGGGCGCCTGTGGTCCCAGCTACTTGGGAGGCTGAGGGAGGAG |
| | AATGGCGTGAACCCAGGAGGCATAGCTTGCAGTGAGCCGAGATTGCACCA |
| | CTGCACTCCAGCCTGGGCAACAGAGCA |

| MAR 17XX_fos core 3' flanking region (SEQ ID NO: 15) | CTCTAGAGCCAGGCACCGTGACTCACTCCTGTGATCCCAGCTTTTCGAAA |
|---|---|
| | GGCTGAGGCAGGAGGATCGCTTGAGGCCAGGAGTTCAAGACCAGCCTTGG |
| | CAACATAGTGAGACTCTCCCGTCTCTAAAACAACAACAACAAAAGGTTAA |
| | TTAAAAATTAAAAGAAAAGAAAACTCCACAGCCACCTTCTCCAGGAAAAT |
| | AAGTCCCAAAGCCACTTGCCACTGATGCAGAGGTGCGCAGAGCCCGAGG |

| MAR 17XX_fos (SEQ ID NO: 16) | GACAGATGGGATTATTCATTTTTATAAAATATTTAACCCAACAAATCCAA |
|---|---|
| | AATATCATTTCAGCATGTAAATAATACAGATGGTCCCCAATTTAACCATG |
| | GTTCCATTAAAGGATTTTTTTTGACTTTAATAATGGATTTATCAGAATAT |
| | AACCTCATCATAAGTTGAGGAACATCTGTATAAAAATATATTAATGAGAT |
| | ACCCTACATTCATTATCCTTTGTATACCAAGTCTTACCATGTGGATTTTG |
| | CACTTCCCACACATCTCAATATGGACCAGCCATATCACGTGCCCCCTGCC |
| | AGATGCATCTAGTGGCTTTCACATCGGACAGCTCCACACTAGAATGACAG |
| | TAAGGCACACGAACCAGACAGTCCCCCCGCTTCCAGCTCCTGATCAACCAC |
| | TTGTAGCCATGGGAGCTTTGGAGACTGCCTTAATAGTTATGAATCTAAGC |
| | TAGGTGTCATGGCTCACACCTGTAATCCCAACTCTTTGGGACGCCAAGAT |
| | GGATGGATAGCTTGAGGCTTTTTTTTTTTTTTTTTTTTTTTTAGACAAG |
| | AGTCTCGCTCTGTTGCCAGGCTGGAGTGCAGTGGCACGATCTTGGCTCAC |
| | TGCAACCTCCGCCTCCCAGGTTCAAGGGATTCTCCTGCCTCAGCCTCCCC |
| | CTGAGTAGCTGAGACTACAGGTGCGCACCACCACGCCCAGCTAATTTTTG |
| | TATTTTTAGTAGAGACAGAGTTTCACCATGTTGGCCAGAATGGTCTCGAT |
| | CACTTGACCTCATGATCCACCCACCTCAGCCTCACAAAGTGCTGGGATTA |
| | CAGGCGTGAGCCACCGCGCCCGGCCAGCTTGACGCTTGAGTCCAGGAATT |
| | CAAGACCAGCCTGGGCAACATGGTCGAAACCCTGTCTCTACTGAAAAAAA |
| | AAAAAAAAAATTATCCGGGCATGGTGACACACGCCTACAGTCCCAGCTAC |
| | CCCAGAGGCTGAGGTGGGAGGATCATTGAACCCCTAAAAGTCAAGGCTGA |
| | AGTGATCCAAGATTGCATCACTGAACTCCAGTCTGGGTGATGGGAGTGAG |
| | ACCCTGTCTCAAAAAAAAAAAAAAAAATAGAAAAGCTCTGAATCTATGGGTT |

TABLE 1-continued

| MAR Sequences | |
| --- | --- |
| Name (SEQ ID NO:) | Sequence |

CTAGCCCTGGGAAATTCTGGATAACATGGAGTTAACAGTTCACCTGCCTC
AGGTGAGATAATGTAAAACTAGAAAGGTCCATACCATTGTGATGTCTAAT
TGAATCTATTTATCAAAACAGTACCCAAATGCAGTATGTTCAGAAACCTT
ATACTGTTAGGTAATAATAACCATAAACAAGATAAAAAATATGGGCTGGG
TGTGGTGGCTCCCACTGTTATCCTAGCATTTTGGGAGGCGAAGGCAGGAG
GATCACTTGAGGCTGGGAGTTTGAGAACAACCTGGGCAACATAGCAAGAC
CCCATCTCTATAAAAAAACATATAAATATAATATAAAGATATATATATTT
TATATATACATATATTTGTACCTGTTAACGTGGGGTGAGGGGTGCAGG
GAGGGTGGAAAGGAGAAAGTCATAATATTAAGCATCAGTAGGCCGGGCGC
AGTGGCTCATGCCTGTAATCCCAGCACTTTGGGAGGCTGAGGCGGGCAGA
TCACAAGGTCAGGAGATTGAGATCATCCTGGCTAACATGGTGAAATATCA
TCTCTACTAAAAATACAAAAAATTAGCCAGGCGTGGTGGCGGGCGCCTGT
GGTCCCAGCTACTTGGGAGGCTGAGGCAGGAGAATGGCGTGAACCCAGGA
GGCATAGCTTGCAGTGAGCCGAGATTGCACCACTGCACTCCAGCCTGGGC
AACAGAGCAGACTCTGTCTCAAATATATATATATTTATATATATATATT
TTATATTTAATATATATAATATATATTATATATAAATTTATTATATATAA
TATATATTATATATAAATTTATTATATATAATATATATTATATATATTAT
ATGTTATATATATTTATTACATATAATATATAATATATATTTATTATATA
TAATATATATTTATTATATATTATATATTATATATTTTATATTTTATATA
TATTATATAATTTTATATTTTATATATATTATATAATTAATATTTAATAT
ATATTATATATATATAAATATATATTTATTATATATAATATATATTT
ATTATATATTTATATATTTATATATTTATATATATTATATATTTA
TATTTTATATATATTTATATATTTATATTTTATATATATTATATATAATAT
ATATATTATATATTTTATATATAATATATATTTATTATACATATTTTATA
TTATATATAATATATTTTATTATATATAATATATATTTTATTATATATTATA
ATATATATATTTATATATATATATTTTATATTTAATATATATAATATATA
TTATATATAAATTTATTATATATAATATATATTATATATAAATTTATTAT
ATATAATATATATTATATATATTATATGTTATATATATTTATTACATATA
ATATATAATATATATTTATTATATATAATATATATTTATTATATATTATA
TATTATATATTTATATTTTATATATATTATATATTTTATATTTTATATATA
TTATATATTTATATTTTATATATATTATATATAATATATATATTATATCT
TTTATATATAATATATATTTATTATACATATTTTATATTATATATAATAT
ATATATTATATATATATATATATATATATTTATATATATATATATTTATA
TATTTTATATATATAATATATATTAATTATATATAATATATATATTAT
ATATATATTATATATAATACGTAATATATATTTATTATATATATTTTGTA
TATATTATATATTATATATTTATTATATATATTTTATATATATTATGTAT
ATTTTATATACAATACATAATATATATTTTATATACAATATATAATATAT
ATTTTATATACAATATAATATATATTTTTATATAATATATTTTTATATA
ATATATATTTTATATTATATATAATATATATTTTTATATATTATATATAAT
ATATATTTTATATTATATATAATATATATTTTTATACTATATATAATATAT
ATTTTATACATTATATAATATATATTTTATACTATATATAATATATATTT
TATACATTATATAATATATATTTTATATATTATATAATATATATTTTATG
TTATATAATATATATTTTATGTATTATATAACATATATTTTATGTATTAT
ATAACGTATATTTTATATATTATGTAACGTATATTTTATATATTATGTAA
CGTATATTTTATATATTATGTAACGTATATTTTATATATTATGTAATATA
TATTTTATATATTATATATTTTGTATATTATATATTTTGTATATGATATA
TTATATATTTTTATATATTATATATTATATATTTTTGTATATTATATATTAT
ATATTTTATATATAATATATCATATATATTTTTATATATATATAAAGCATC
AGTAAACAACTCTAGAGCCAGGCACCGTGACTCACTCCTGTGATCCCAGC
TTTTCGAAAGGCTGAGGCAGGAGGATCGCTTGAGGCCAGGAGTTCAAGAC
CAGCCTTGGCAACATAGTGAGACTCTCCCGTCTCTAAAACAACAACAACA
AAAGGTTAATTAAAAATTAAAAGAAAGAAAACTCCACAGCCACCTTCTC
CAGGAAAATAAGTCCCAAAGCCACTTGCCACTGATGCAGAGGTGCGCAGA
GCCCGAGGAACACGGAGTCATAGCAGCTCTGCAAATTGATTTTATTCCAG
GCTAAAAGATGCTATTTCTCAAAAAAAGGAGCTGGGAGCGTCTCTGTTCA
TGAATTCATTTTTCAGGGGTGGGGTGATTTCAAGAGTCCAGGCTGTTTCC
TGACCATGCACACTGTTCCGGCCTGGAAGCCTCAGACCCCAGCCAGGCTG
ACCACGAGCCAGACCCGGAGTAAGCTTCGTCCCATGCTTCCTGTCGGTCC
GGGCAGCCTGAGTTTCCTGGTGACCCTTCCCTGCACCCAGCCAATTCAAA
GGTCTGGCAAGGCCTGGTGCCAGCCAAGAAAATCTGAGGCAGCCAGGTTT
GTTATTTCAAATCTCTAAACCTTCAGACCTCTGTGCTTGGCTTACATATG
TGAAAGTTAAAACAAGGATGTGTGTCGCAGTGGTGATTATAATTCAAGTA
AGCAAAGATCCCTGCATGACCAGCCTTCGAATGTCAGCCCATGCTGAAGT
TAACACATTTAACTCATAGAACAAAATAGTTAAAATGAGGAGTGGATGCA
AAATGGTACTGCCATTCTAGAAAACAGTTGGCAGTTTCTTATAAAGTTAA
ACGTACGCTTACCACAAGACCCAGCAATCACCCTCCCAGAGAAATGAAAA
TTTATGTTCATATAAAATATTGTACACAAATAATTATAACAGCTTTATTT
GTAATAGTCATGTATCAATCAGGATTCTCCAAGGAAACAGGACCAATAGA
AGAGAGATATATACATAATAAATCATATATATAAATGATATATATAAGAA
GTTATATATATATACACAAACACATACATATATTGTGATAACCTACCTTG
TTTTAACCTGAGTGACTCTCTCCTAGCAGAGAGAGCCAGACAGACTCCAT
TTTAGTTTCTTCATTCACAGCCCCCTTTATCCCCCTTAAGGGAATAACTA
GTGCAAGCTGACTCTAAGCACATCCAGTAATGCACCTGCTGATAAGATAT
TGAGGCAGGCTGTACCAGCAGCTCCTGGGAATGTGCTCGGTGGAAGGTAT
CTAAAAGCCCCTGCATTTATCTCTTAGTGATAGTTTAAGCCCCTGCACCT
GGAACTGTTTATCTTTTACAACTGCTTCTATAACCAATTAATTTTTTAAC

TABLE 1-continued

MAR Sequences

| Name (SEQ ID NO:) | Sequence |
| --- | --- |
|  | TTTTTGCCTGTTCTGCTTCTGTAAAACTGCTTCAGTTAAACTCCCCCTCC |
|  | CCTATTTAGACCATAGTATAAAAGAGAATCTAGCCCCTTCTTCGGGGCTG |
|  | AGAGAATTTTGAGTGCTAGCTGTCTCTCAGTCGCCGGCTAATAAAGGACT |
|  | CCATAATTTGTCTCAAAGTGTGGCGTTTCTCTATAACTCGCTTGGTTACA |
|  | ACACTATCTCTCAGGGATCTCCAAAGAAATAGAACCTATAGGATATATCT |
|  | ATCTATAATAAATCATTGCCAGGCATGGTGGCTCACCCAGTACTTTGGGA |
|  | GGCCAAGTCAGGAGGATCACTTGAGCCCAGGAGTTTGAGGCCACCTGAGC |
|  | AACATAGTGAGACCCTGTCTCTAC |
| MAR 1_68 core (SEQ ID NO: 17) | CCAGCTACTCGGGAGGCTGAGGCAGGAGAACGGCTTGAACCCAGGAGGTG |
|  | GAGGTTGCAGTGAGCTGAGATCGCGCCACTGCACTCCAGCCTGGGCGACA |
|  | GAGCGAGACTCTGTCTCAAAAAAAAAATATATATATATATATATATACAC |
|  | ATATATATATAAAATATATATATATACACACATATATATATAAAAATATAT |
|  | ATATATACACACATATATATAAAATATATATATATACACACATATATATA |
|  | AAATATATATATACACACATATATATAAAATATATATATACACACATATA |
|  | TATAAAATATATATACACACATATATATAAAATATATATATACACACA |
|  | TATATATAAAATATATATATACACACATATATATAAAATATATATATACA |
|  | CACATATATATAAAATATATATATACACACATATATATAAAATATATATA |
|  | TACACACATATATATAAAATATATATATACACACATATATATAAAATATA |
|  | TATATACACATATATATAAAATATATATATACACACATATATATAAAATATT |
|  | TATACACACATATATATAAAATATATATATACACACATATATATAAAATA |
|  | TATATATACACATATATATAAAATATATATATACACACATATATATAAAATA |
|  | TATATATACACATATATATAAAATATATATATACACACATATATATAAAG |
|  | TATATATACACACATATATATAAAATATATATATACACACATATATATAA |
|  | AATATATATATACACACATATATATAAAATATATATATACACATATATATAA |
|  | AAATATATATATATATTTTTTAAAATATTCCAATTGTCTCACTTTGTGGA |
|  | TGAGAAAAGAAGTAGTTAGAGGTCAAGTAACTTGGCCTACATCTTTTCT |
|  | CAAGATTGTAAACTC |
| MAR 1_68 5' flanking region (SEQ ID NO: 18) | CTGTGCTCCCTTAACATCCTATTTTATCTGTATATATATATATTCTTCCA |
|  | AATATCCATGGGAAAAAAAATCTGATCATAAAAATATTTTAGGCTGGGAG |
|  | TGGTGGCTCACGCCTGTAATCCCAGCACTTTGGGAGGCTGAGGTGGGCGG |
|  | ATCATGAGGTCAAGAGATCGAGACCATCCTGACCAATATGGTGAAACCCC |
|  | ATCTCTACTAAAGATACAAAACTATTAGCTGGACGTGGTGGCACGTGCCT |
|  | GTAGTC |
| MAR 1_68 core 3' flanking region (SEQ ID NO: 19) | CTAGTGAGCAATAACCACATCTTCATTTTCTTTGTATAAAACAAGAAAGT |
|  | TTAGCATGAAAAAGGTACTCAATTACAAATGTGTTGGATTGAATTGAAGA |
|  | CCCTTGGAAGGGGATTTTGTACCTGAGGATCTCTTTCTTTTGGCCATATT |
|  | GTTCAATGGACAAAATTTAGCCTTCGAAGGCAGGCCGATTTGAGGTTAAT |
|  | ACTACCTTTACCACTTGATAGCTATGTGACCTTGGCCATG |
| MAR 1_68 (SEQ ID NO: 20) | GACTCTAGATTATACCAACCTCATAAAATAAGAGCATATATAAAAGCAAA |
|  | TGCTCTTATCTTGCAGATCCCTGAACTGAGGAGGCAAGATCAGTTTGGCA |
|  | GTTGAAGCAGCTGGAATCTGCAATTCAGAGAATCTAAGAAAAGACAACCC |
|  | TGAAGAGAGAGACCCAGAAACCTAGCAGGAGTTTCTCCAAACATTCAAGG |
|  | CTGAGGGATAAATGTTACATGCACAGGGTGAGCCTCCAGAGGCTTGTCCA |
|  | TTAGCAACTGCTACAGTTTCATTATCTCAGGGATCACAGATTGTGCTACC |
|  | TATTGCCTACCATCTGAAAACAGTTGCTTCCTATATTTCATCCAGTTTAA |
|  | TATTTATTTAAACCAAGAAGGTTAATCTGGCACCAGCTATTCCGTTGTGA |
|  | GTGGATGTGAAAGTACCAATTCCATTCTGTTTTACTATTAACTATCCTTT |
|  | GCCTTAATATGTATCAGTAGGTGGCTTGTTGCTAGGAAATATTAAATGAA |
|  | TGGCATGTTTCATAGGTTGTGTTTAAAGTTGTTTTTTGAGTTAAATCTTT |
|  | CTTTAATAATACTTTCTGATGTCAAAAACACTTAGAAGTCATGGTGTTGA |
|  | ACATCTATATAGGGTTGGATCTAAAATAGCTTCTTAACCTTTCCTAACCA |
|  | CTGTTTTTGTTTGTTTGTTTTTAACTAAGCATCCAGTTTGGGAAATTCTG |
|  | AATTAGGGGAATCATAAAAGGTTTCATTTTAGCTGGGCCACATAAGGAAA |
|  | GTAAGATATCAAATTGTAAAAATCGTTAAGAACTTCTATCCCATCTGAAG |
|  | TGTGGGTTAGGTGCCTCTTCTCTGTGCTCCCTTAACATCCTATTTTATCT |
|  | GTATATATATATATTCTTCCAAATATCCATGGGAAAAAAAATCTGATCAT |
|  | AAAAATATTTTAGGCTGGGAGTGGTGGCTCACGCCTGTAATCCCAGCACT |
|  | TTGGGAGGCTGAGGTGGGCGGATCATGAGGTCAAGAGATCGAGACCATCC |
|  | TGACCAATATGGTGAAACCCCATCTCTACTAAAGATACAAAACTATTAGC |
|  | TGGACGTGGTGGCACGTGCCTGTAGTCCAGCTACTCGGGAGGCTGAGGC |
|  | AGGAGAACGGCTTGAACCCAGGAGGTGGAGGTTGCAGTGAGCTGAGATCG |
|  | CGCCACTGCACTCCAGCCTGGGCGACAGAGCGAGACTCTGTCTCAAAAAA |
|  | AAAATATATATATATATATATATACACATATATATATAAAATATATATAT |
|  | ATACACACATATATATATAAAATATATATATACACACATATATATAAAA |
|  | ATATATATATACACACATATATATAAAAATATATATATACACACATATA |
|  | TATAAAATATATATATACACACATATATATAAAATATATATATACACACA |
|  | TATATATAAAATATATATATACACACATATATATAAAATATATATATACA |
|  | CACATATATATAAAATATATATATACACACATATATATAAAATATATATA |
|  | TACACACATATATATAAAATATATATATACACACATATATATAAAATATA |
|  | TATATACACACATATATATAAAATATATATATACACACATATATATAAAATA |
|  | TATATATACACACATATATATAAAATATATATATACACACATATATATAAAATA |

TABLE 1-continued

MAR Sequences

| Name (SEQ ID NO:) | Sequence |
|---|---|
| | TATATATACACATATATATAAAATATATATACACACATATATATAAAATA<br>TATATATACACACATATATATAAAATATATATATACACATATATATAAAA<br>TATATATATACACATATATATAAAATATATATATATACACATATATATAA<br>AATATATATACACACATATATATAAAGTATATATATATACACACATATATAT<br>AAAATATATATATACACATATATATAAAATATATATATACACATATATAT<br>AAAATATATATATACACATATATATAAAAAATATATATATATATTTTTTAA<br>AATATTCCAATTGTCTCACTTTGTGGATGAGAAAAAGAAGTAGTTAGAGG<br>TCAAGTAACTTGGCCTACATCTTTTCTCAAGATTGTAAACTCCTAGTGAG<br>CAATAACCACATCTTCATTTTCTTTGTATAAAACAAGAAAGTTTAGCATG<br>AAAAAGGTACTCAATTACAAATGTGTTGGATTGAATTGAAGACCCTTGGA<br>AGGGGATTTTGTACCTGAGGATCTCTTTCTTTTGGCCATATTGTTCAATG<br>GACAAAATTTAGCCTTCGAAGGCAGGCCGATTTGAGGTTAATACTACCTT<br>TACCACTTGATAGCTATGTGACCTTGGCCATGTGGTTTCAACAGTCTGAA<br>CCTCATTTTCTCTGTGTATGTGTGGTCCTCCTTACAAGTTTGTGAAAAAT<br>GTGAAGTCCTTAGCCATGATAGCCCAATATAACAGGCTAAATGATAATAG<br>GTTTATGTTCTTTTCCTTTATATTCTCAGATAAGCACTGTCCAAGTTTGA<br>GGTGTTTTGAGGTCTCGCCTGATTTGGATTGTTTGAGTTTATGCTATTCT<br>TTGAATTCTTTGAGCTGTTCTGAAGCAGTGTATCATGAACAAAAACATCC<br>CCAGTTCAGTCCAAACCCCTGGTTACATATCATTCTTATGCCATGTTATA<br>ACCAGTTTGAGAGTGTTCCCTCTGTTATTGCATTTAAGTTTCAGCCTCAC<br>ACAGAAATTCAGCAGCCAATTTCTAAGCCCTAAGCATAAAATCTGGGGTG<br>GGGGGGGGGGATGGCCTGAAGAGCAGCATTATGAATAGCACCATTATAAT<br>TAATGATCTCTCAGGAAGATTTACAATCACAGGTAGCAGATAAAACAAAT<br>AGTACTGCTTCTGCACTTCCCCTCCTTTTATTCGCTATGAAATTTTATGG<br>GAAATCAGTCCAGTGAAAAATGTAAGCTCTTAATCTTTCCCAGAAATCCT<br>ACCTCATTTGATGAATACTTTGAGGGAATGAATTAGAGCATTTTTTTCTT<br>TTATAGTCTACTTCGCATTTACGAAGTGAGGACGGTAGCTTAGGCTGCCT<br>GGCCAACTGATGAGAAGGTCAGAGGCATTTTTAGAGACCTCTGTTGTCTT<br>TCATTCATGTTCATTTTCCACAAGGCAAGTAATTTCCAACAAATCAGTGT<br>CTTCATTAGTAATAAGATTATTAACAACAATAATAGTCATAGTAACTATT<br>CAGTGAGAGTCCATTATATATCAGGCATTCTACAAGGTACTTTATATACA<br>TCTGAGTAAACCTCACACAATTCTACAGGGAGGTATTTCTATCCCCATTT<br>AACAAATAAGGAAACGAAGTCCAAGTAAATTAACTTGCCCAAGGTCACAC<br>AGATAGTACCTGGCAGAACAGGAATTTAAACCTAAATTTGTCCAACTCCA<br>AAAGCAGCCTTCTATTTGTTATAAATGCTGCCTCTCATTATCACATATTT<br>TATTATTAACAACAACAAACATACCAATTAGCTTAAGATACAATACAACC<br>AGATAATCATGATGACAACAGTAATTGTTATACTATTATAATAAAATAGA<br>TGTTTTGTATGTTACTATAATCTTGAATTTGAATAGAAATTTGCATTTCT<br>GAAAGCATGTTCCTGTCATCTAATATGATTCTGTATCTATTAAAATAGTA<br>CTACATCTAGAG |
| MAR S4 core (SEQ ID NO: 21) | ATATGTATATATGTATATATGTATATATGTATATATGTATATATGTATAT<br>ATGTATATATGTATATATGTATATATGTATATATGTATATATGTATATAT<br>GTATATATGTATATATGTATATATGTATATATGTATATATGTATATATGT<br>ATATATGTATATATGTATATATGTATATATGTATATATGTATATATGTAT<br>ATATGTATATATGTATATATGTATATATGTATATATGTATATATGTATAT<br>ATGTATATACGTATATATGCATATACGTATATATGTATATATGTATATAT<br>GTATATATGTATATATGTATATATGTATATATGTATATATGTATATATGT<br>ATGTATGTATGTATGTATGTATATATGTATATATGTATGTATGTATGTAT<br>GTATGTATGTATGTATATATGTATATATATGTATGTATGTATGTATGTGT<br>ATGTATGTATATGTGTATATGTGTATATGTGTATATGTGTATATGTGTAT<br>ATATGTATATATGTATATATGTATATATGTATATGTGTATATGTGTATAT<br>GTGTATATATGTATATATGTATATATGTATATATGTATATATATAACAT |
| MAR S4 5' flanking region (SEQ ID NO: 22) | GCTCTTTCCTTTAGTTAAGCTTATGAAATAGTGTTTCTCTCATGTTTCCT<br>CTATATTCTCTCTTTTGCCTTCCTGTTTCTTCCTGTTGATTCCATCCCAT<br>TGGAGTGAAATCTTATGATCTTTTGGCATCAACAAAGTGATCTGCATCCA<br>AATAATTCCACATCTCATTCCATGTTGACTGTGGATCTATATATATATAT<br>ATGTA |
| MAR S4 core 3' flanking region (SEQ ID NO: 23) | AGTATTAAATTATATATACATATATAAGTGAAATGTCACAATCTTCTAGA<br>ACTTGCTCTGTATGTCCACTTAACATGGTAGAGTGAGCTATGTCAGCATT<br>TTCTATTTCCTGTGAATCATTCTGTGTGTTGCCAAGAGAAATATGATTAT<br>ATTCTGAGGTTATGAAATGATATTTTGGTCATCATGTTTCTCATCCTATT<br>TTCATATTACCTAAATACTTTTGCTTTTAAAATTATTATTATTAATAATA<br>ATATAATTATTTATACAATAATATTTAAATAATATATTTATTTAATATAA<br>TTATTATATTTCACATAAAAGCAATAGTTCCAGTGTTACAAATTGTAGGC<br>AA |
| MAR S4 (SEQ ID NO: 24) | CTCGAGGTCTCAAGATAAGAATGACTGCTGTAACTCAAATCCACCAAAGC<br>TATTTGTGTTAGAATGCTTTCCTTTGGTAATAACATAATACCACAGAGTG<br>AGTGAATGTATCAAGCAAAGTACTCACTCATAATCTCTCCACCCAAATGA<br>CTTTGTCTTCTAAAATTAAACCCTTCCCAGAGGCCTCTCCCCTTAATACC<br>ATATTGGGCTCTTCACACTTCTTCCAACATCGCCTTCCATCCTGGCCCTT<br>CCAACCTCCCTTCTGTTTGTGCTAGGAACAGCTCAAGGCCTCCTATCTAC<br>CACAGAGTTACATGGCTTGCCCCTTGCCAACCCCCCAGTACCACACAGTG |

TABLE 1-continued

| | |
|---|---|
| | MAR Sequences |

| Name (SEQ ID NO:) | Sequence |
|---|---|
| | AGTGCAAAATCTCACCACATTCAGAACCCAGTCACTATTCAAATCATATT |
| | TTAACCTTTGCAGTACTGACTACTTTTGATTCATCTAAACATTACTGAAC |
| | TTTATTCTAGAAAACATTTAAGAAATTTGTAGTTAGGTTCATCCTTTGAG |
| | ACCTTACATTTAATTTCTTTCTATGTAAACGGAAAGCATTGTTCAGTCCC |
| | ACGCTCATTATGGCAACCCACTTCCAAGTACTTCGTTTACTACGTGGGCT |
| | GGAATCATACAGTTTTCTGTTGTGCTTGTGGGAGCAGATCCCCCTAACCT |
| | CTGCTGATTTTTCTCACCACTTATCATACATTTATTACATGCATGCACTG |
| | CTGTGTGAGTTTCTAAATACTTGGGTAGCAATTCTCTACTATTACTTTAA |
| | TTTTCCTACTTGTCTGCAAATACGAAAAGTAGCTTGAAAGAACTTCAGAT |
| | CTTTGTTGTTATCTGTTGCAAACACTCCATTTTTCTGTTGTAGCAAAAAA |
| | AAAAAAAAAGACATCCATAGTTGTCAATGAGAATGCAAGATACATACATT |
| | CTGCACCTGTGTGCTAACATAAGTGGCTGCCCTGTGACTCAGAGATTGCT |
| | TGTCCTTCTCCTAAGCCTATCCTTTTTTGTTACTTTGGATACTTTTGTTC |
| | AATGAATCCAGAAAAAGTGTTTTTCAGATTCACCATGTGACCCTCATTTA |
| | AAACCTGTAATCCCCCTATGGTTAAGTTCCTGCTTTTGTTTCTGTTTTCT |
| | TTCTTTCAGTAAAAGGAATTGAACCCAGTCCTTCCACTTACTATCTGAGC |
| | ATATGGCTCTTTTAGATTATGATGTTGGTGGTGTTCATTGGTCTCACCAA |
| | AATGCTAAAGAAGCCTTCATCTTCTACTTGTGGGTAGTCTTTACATTCAT |
| | TACTGCAAGTTTAGTTTATGTGGTAGTACCAGATCCTTTGCTTCTTTTGA |
| | CTTCATGCCTACCTAACAGCGCTCTTTCCTTTAGTTAAGCTTATGAAATA |
| | GTGTTTCTCTCATGTTTCCTCTATATTCTCTCTTTTGCCTTCCTGTTTCT |
| | TCCTGTTGATTCCATCCCATTGGAGTGAAATCTTATGATCTTTTGGCATC |
| | AACAAAGTGATCTGCATCCAAATAATTCCACATCTCATTCCATGTTGACT |
| | GTGGATCTATATATATATATATGTAATATGTATATATGTATATATGTATA |
| | TATGTATATATGTATATATGTATATATGTATATATGTATATATGTATATA |
| | TGTATATATGTATATATGTATATATGTATATATGTATATATGTATATATG |
| | TATATATGTATATATGTATATATGTATATATGTATATATGTATATATGTA |
| | TATATGTATATATGTATATATGTATATATGTATATATGTATATATGTATA |
| | TATGTATATATGTATATATGTATATATGTATATACGTATATATGCATATA |
| | CGTATATATGTATATATGTATATATGTATATATGTATATATGTATATATG |
| | TATATATGTATATATGTATATATGTATGTATGTATGTATGTATGTATATA |
| | TGTATATATGTATGTATGTATGTATGTATGTATGTATGTATATATGTATA |
| | TATATGTATGTATGTATGTATGTATGTATGTATATGTGTATATGTGTA |
| | TATGTGTATATGTGTATATGTGTATATGTATATATGTATATATGTATGTATA |
| | TATGTATATGTGTATATGTGTATATGTGTATATATGTATATATGTATATA |
| | TGTATATATGTATATATATAACATAGTATTAAATTATATATACATATATA |
| | AGTGAAATGTCACAATCTTCTAGAACTTGCTCTGTATGTCCACTTAACAT |
| | GGTAGAGTGAGCTATGTCAGCATTTTCTATTTCCTGTGAATCATTCTGTG |
| | TGTTGCCAAGAAGAAATATGATATATTCTGAGGTTATGAAATGATATTTT |
| | GGTCATCATGTTTCTCATCCTATTTTCATATTACCTAAATACTTTTGCTT |
| | TTAAAATTATTATTATTAATAATAATATAATTATTTATACAATAATATTT |
| | AAATAATATATTTATTTAATATAATTATTATATTTCACATAAAAGCAATA |
| | GTTCCAGTGTTACAAATTGTAGGCAATGGGCTGTTCTGATTATCTAAGTT |
| | GGGCCCAGGATATGTGCTGAATAGTTAAAGCACATGCCCAGCATGTATGA |
| | GGGTAAAAGGATGGGTGGATGTAGTGACCCATTTGTAATTTAAGCCTTAG |
| | CAGGCAGAGGTGTGACCCATAGTGCAAAGTACATAGTCATTATAAGGTCA |
| | TCTATATCACAATCTCTGGATTAGATTGATTGAACCTGCTCAGTGACCAA |
| | TGTGTTAGCAATATACAGGAGGATGATAACATCAACGTCAGAAGACACAT |
| | TGAAGGGCTTACAAATAGTGCCCATTTACTTTAATACAGAAAAATTCAAT |
| | GTACCCTCTAGGCAATTTCAACTTTTAGTCTCTTGGTAGGATAGTCTACA |
| | TTTAGAATGGCTAATTCATAAATTAGAAAGCTTCTTCACCCCCTACTTTT |
| | CTGGTTATTTCTCTATGAATGTGGTAGGCATGAGTTAGTACACATGTTTC |
| | CATGTACATGTGTTTCTATGTGTCTGCATGCATATGGTAGAATGTACTCA |
| | TATTCTATGTACAGTTAGAACAATATTTATATTGTCAAAGAAATCAAAAG |
| | GAGTATTATAAGCTTCAGAAATAAGGATAAGTTTGAAATATTCATTGTTT |
| | TATTTTTTACAGTATTTTTTCCTTTGAGAATTCTATGTAAAGTACTTTGA |
| | ACATATTTGCCTTCAACTCCTCCCTCACTTTCACCCTCTCTTCATTCCTC |
| | CCTTTCCTTTCCACTCAAAGTTGAGATTCCTTTATTTATTTATTTATCCT |
| | TCAAATATCACTGGTACTATCCACATGATCTCAGGATTGAGGTCTGCTCT |
| | GACGTGTCATCCTGCTTTCATGCAATGGCCTTATAGGTGGAACAACATTA |
| | TGAACTAACCAGTACCCCGGAGCTCTTGACTCTAGCTGCATATATATCAA |
| | AAGATGGCCTAGTCGGCCATCACTGGAAAGAGAGGCTCATTGGACTTGCA |
| | AACTTTATATGCCCCAGTACAGGGGAACACCAGGGCCAAAAAGGGGGAGT |
| | GGGTGGGCAGGGGAGTGGGGGTGGGTGGATATGGGGGACTTTTGGTATAG |
| | CATTGGAAATGTAAATGAGTTAAATACCTAATAAAAAATGGAAAAAAAA |
| | GTTTCTAATGTGTGTTTCTAGAAACTTCCTCTCTTAAAGCAACAACATGT |
| | CCATGAGCAATATAGAATTGAAGATCACCATCAAATCCTCTTTATTCCTC |
| | ATTGTTTCCATCATGTACTACCAGACCTCTTTAAAGTGTAGTACAGTGTG |
| | TTAGGAAATGAGCAGATTATCCTGGGTATGTGCTAAATTAGCTACTGAGT |
| | CAAAATACATTTTTTGCTGAACATTAAGTGTTTGGTCATTTCTGGGCAAA |
| | AGAAAGAAAGAAAGAAAGAAAAGAAAGAAAGAAAGGAAGGAAGGAAGGAA |
| | GGAAGGAAGGAAGGAAGGAAAGAAGGAAGGAAAGAAAAAATGGATGTAAA |
| | TTGTTCTGACAGCATCTGTCTGAGTCAGGCAGTGGAATGAAGGAGGAATC |
| | CTAGAGAATGCACAGGAAAGCAGCCCAAGGAGAGTGTGGGCTGAAAGGCA |
| | TCATGTTAGAAACATGCACTCGATGACAGAACCTTGAGAAAAAGGAACTC |
| | AAGCAAAAGCACTTATTTAAAATTGTAAAACGCACTTTATTCATAGCCAT |

TABLE 1-continued

| MAR Sequences | |
|---|---|
| Name (SEQ ID NO:) | Sequence |

|  |  |
|---|---|
|  | GGGGGATGTCAATATTCCAAGCATAAGAATGATCAGTTTCCAATCACTGT |
|  | GAACCCCCAAAACACAAAGTGAAAACCCACTACTTTATTTGATGAGATTT |
|  | GGGGTTGCTCTATTAATTTATAAAATCAGAGTAAGACACGATATAAATGA |
|  | AACGATTGTAGTTCTAAAGCAGCGGCACTTCCCTGAACAGTGTCATTTTG |
|  | ACAAGTAACTGCTAACATCTTCAGGTCACAGCGACTGAAGAAAAAGTAGG |
|  | GAAAGAAGGCTGGCTGTGCTGTTTGACATTTTCTTTTCTTATCTGGTGAC |
|  | ATGAAGAGAAGCTCTGGGTCCCCCTACTCTTGTTCATATATCTGTTGCTT |
|  | TTATGCTGCATCCTGAGGTTTGAAGAAATGCATTTGGCACTGAGAAAAGA |
|  | TGAGGAGAGAATGCCTTGGACATGGTCCTAACATGCTTTGGTACTGAGAA |
|  | AAGAGAGCAGAGGAGATGACATAGAATAGGAGAGATAATTTGGCCTATTT |
|  | TGGCCTTCATCTGAGTGATAGATTTTACTTAACAAATAGAAACAAAGTTT |
|  | TACTTATAAACAGAACCAATGACCTGTGTCATCTCTGATATATTGAGCTT |
|  | TGAATTCAGTGAAATTATGAACTAAATATATCACTCCATAATTTTCTAAG |
|  | AGGGCTATTTGTATAGTTTCAGTGATAGTGTGACAAAGTGTAATCTAAAT |
|  | TTCTAAAAAGTAAAATAAGTAGATAAAATAGTAGGTAGAATAGTATAATA |
|  | ATAGAATAAGTATAGGTATGGACTAGAATAAATAGACAAAATAGTAGATA |
|  | AAATGCTAATGATTTTGTTGACAGGGTAATCATGAATATTTTTATTATTT |
|  | AGCTAAAGAACCAATGTTCATGTACTCAAGAAGTGTATTGAGGAACTTAG |
|  | GAAATTAGTCTGAACAGGTGAGAGGGTGCGCCAGAGAACCTGACAGCTTC |
|  | TGGAACAGGCGGAAGCACAGAGGCACTGAGGCAGCACCCTGTGTGGGCCG |
|  | GGGACAGCCGGCCACCTTCCGGACCGGAGGACAGGTGCCCGCCCGGCTGG |
|  | GGAGGCGACCTAAGCCACAGCAGCAGCGGTCGCCATCTTGGTCCGGGACC |
|  | CGCCGAACTTAGGAAATTAGTCTGAACAGGTGAGAGGGTGCGCCAGAGAA |
|  | CCTGACAGCTTCTGGAACAGGCAGAAGCACAGAGGCGCTGAGGCAGCACC |
|  | CTGTGTGGGCCGGGGACAGCCGGCCACCTTCCGGACCGGAGGACAGGTGC |
|  | CCACCCGGCTGGGGGAGGCGGCCTAAGCCACAGCAGCAGCGGTCGCCATCT |
|  | TGGTCCCGGG |
| MAR X29 core (SEQ ID NO: 25) | TAGGCAACAGAGTGAGATCATGTGTCATATATATATATATATATATATAT |
|  | ATATATATATATATACACACACACACATATATATATACACATATAT |
|  | ATACGTATATATATATGTATATATATACATATATATACATATATATAT |
|  | ATACGTATATATATACGTATATATATATCAATGTAAATTATTTGGGAAAT |
|  | TTGGTATGAATAGTCTTCCC |
| MAR X29 5' flanking region (SEQ ID NO: 26) | AAATACAAAAATTAGCCAGGTGTGGTGGCATGTGCCTGTAGTCCTACCTA |
|  | CTCGGGAGGCTGAGGCACAAGAATCGCTTGAATGTGGGAGGTGGAGGTTG |
|  | CAGTGACCTGAGATCGTGCCACTGCACTCCAGCC |
| MAR X29 core 3' flanking region (SEQ ID NO: 27) | TGTGAACACAGATCATAAAATCATATATCAAGCAGACAAATAAGTAGTAG |
|  | TCACTTATATGCTTATACTTGTAACTTAAAGTAAAAGAATTACAAAAGCA |
|  | TATGACAAAGACTAATTTTAAGATATCCTAATTTAAATTGTTTTCTAAAA |
|  | GTGTGTATACCATTTTACCTATCATATGAATAATTTAGAAACATGTTTAT |
|  | AAAATTAATGTCCAAATCCATTCAAAAGTTTTGTAATGCAGATCAC |
| MAR X29 (SEQ ID NO: 28) | AGCGCCGAATTCGATCCCTTTATAAAACCACAATATAATGGAGTGCTATA |
|  | ATTTCAAACAGTGTTTGGTCTGCTGGCAGAGTGGTCATTCTAACAGCAGT |
|  | CACAGTAGAGTAGAAATAAGACTGCAGTATATCTAAGGCAAAAAGCTGAG |
|  | GTTTCAGGAGCTTGAAGGTAAAGAGGAAGAAAGAAATGGGAATGGGAATT |
|  | GGAAAGACAAATATCGTTAAGAGAAAATTGCTTTTAGGAGAGGGGAAAGA |
|  | ATCTATGTGTACTTAAGACTATGGAATCAATCCCATTTAAGCTGGGAAAC |
|  | TAGTTTCATATATAACTAATAAATTTTATTTACAGAATATCTATTTACCT |
|  | GATCTAGGCTTCAAGCCAAAGGGACTGTGTGAAAAACCATCAGTTCTGTC |
|  | ATATTCCTAAAAAAAAAATTAAAAAGTTAAAAATAAATAAATAATAAAACT |
|  | TCTTTTCTTTCAAAATAATCAAGGTGCTTATTCACATCCATTCCAATTTG |
|  | GGGAAATACTTATTTTCCTATGATTAGCGAAGAGAAAAGTAACTTGCATT |
|  | TCAATTCAAGTTGATACATGTCACTTTTAAGAGGTCAACTAATATTTGCT |
|  | AGTTGAGCTAACCATATAGGCTTTAAATACTTTCATAGTAGAAAGAAAAT |
|  | GAAAATCATTAGTGAACTGTATAAAATAGATCATACTTTTTGAAAGAATC |
|  | AGACTGAAGTTTCCGAAAAAAAGAAGTAAGCTTCAATGAAAAGGTAAGTG |
|  | AATTTAGCATTTACTCAGCATCTACTATGGACTTAACACCTAACAGTAGA |
|  | TAATCTGAAGGCAAACATATTTGTATAGGGACTGCAGAATGATAGATGAT |
|  | AAATATCATCTCTTCTATTTGAATGAATATTTTTTCAAATCTTTCACACA |
|  | CAGTGGTTTGCTATGGAAAGATTTGTAGTACATTAAACAAATCTGAAGAT |
|  | GGAGTTAGAAAGCTTAGGCTATGTTTTGAGCACAACATATAAATTTCTCTG |
|  | TGATTGTTTCTTCATCTTTCAAATGAGGTTACTGTGAAGATTAAATGAGA |
|  | TAACTAAATGATGATAAAATAATGTAATCTTAGCAGCACCTTATTTAATC |
|  | TGTGCAACAACTCTGTGAAGTGAGTAGGGCTCAGCTTCAGTCACTTCTCT |
|  | GCCATTTATTAACTAAGATAGTTTGGAAAGTTACCCATCTCTTCAGCTGT |
|  | AAAATGATGAGGATCATACCTATTTTATGGGGCTGCTTTTAGGTACAAAT |
|  | ATACAGGCAAGCACTTTGTTAATACTAAAGCATTACACCAATTAGTTTTA |
|  | CTCTTTTCCATTCACACATGAAATTAATGTAATCAGAATTCTGTAGATTA |
|  | CCTAAATCTTCTGTTAACACGTGATATGCAGTTCAGGTTAAATGTCAGTT |
|  | GAGTTACCAAAGCACATACATACTCACCACCCTATCCAAATCTACAAGCC |
|  | TCCCAGTTTGTCTTCACTATTTTGGTTAAATTAATATGAATTCCTAGATG |
|  | AAAATTTCACTGATCCAAATGAAATAAAAAATATATTACAAAACTCACAC |
|  | CTGTAATCTCAACATTTTGGGAGGCCAAGGCAGGTAGATCACTTGAGGCC |

TABLE 1-continued

| | MAR Sequences |
| --- | --- |
| Name (SEQ ID NO:) | Sequence |

| | |
| --- | --- |
| | AGGAGTTCAAGACCAGCCTGATCAACATGGTGAAACCCTGTCTCTACTAA<br>AATACAAAAATTAGCCAGGTGTGGTGGCATGTGCCTGTAGTCCTACCTAC<br>TCGGGAGGCTGAGGCACAAGAATCGCTTGAATGTGGGAGGTGGAGGTTGC<br>AGTGACCTGAGATCGTGCCACTGCACTCCAGCCTAGGCAACAGAGTGAGA<br>TCATGTGTCATATATATATATATATATATATATATATATATATATATATA<br>CACACACACACACATATATATATACACATATATATATACGTATATATATATA<br>TGTATATATATACATATATATACATATATATATATACGTATATATATACG<br>TATATATATCAATGTAAATTATTTGGGAAATTTGGTATGAATAGTCTT<br>CCCTGTGAACACAGATCATAAAATCATATATCAAGCAGACAAATAAGTAG<br>TAGTCACTTATATGCTTATACTTGTAACTTAAAGTAAAAGAATTACAAAA<br>GCATATGACAAAGACTAATTTTAAGATATCCTAATTTAAATTGTTTTCTA<br>AAAGTGTGTATACCATTTTACCTATCATATGAATAATTTAGAAACATGTT<br>TATAAAATTAATGTCCAAATCCATTCAAAAGTTTTGTAATGCAGATCACC<br>CACAACAACAAAGAATCCTAGCCTATTAAAAAAGCAACACCACCTACATA<br>TAATGAAATATTAGCAGCATCTATGTAACCAAAGTTACACAGTGAATTTG<br>GGCCATCCAACACTTTGAGCAAAGTGTTGAATTCATCAAATGAATGTGTA<br>ATCATTTACTTACTAATGCCAATACACTTTAAGGTAATCTTAAGTAGAAG<br>AGATAGAGTTTAGAATTTTTTAAATTTATCTCTTGTTGTAAAGCAATAGA<br>CTTGAATAAATAAATTAGAAGAATCAGTCATTCAAGCCACCAGAGTATTT<br>GATCGAGATTTCACAAACTCTAACTTTCTGATACCCATTCTCCCAAAAAC<br>GTGTAACCTCCTGTCGATAGGAACAACCCACTGCAGGGATGTTTCTCGTG<br>GAAAAAGGAAATTTCTTTTGCATTGGTTTCAGACCTAACTGGTTACAAGA<br>AAAACCAAAGGCCATTGCACAATGCTGAAGTACTTTTTTCAAATTTAAAA<br>TTTGAAAGTTGTTCTTAAAATCTATCATTTATTTTAAAATACGGATGAAT<br>GAGAAAGCATAGATTTGATAAAGTGAATTCTTTTCTGCAATCTACAGACA<br>CTTCCAAAAATCACTACAGACACTACAGACACTACAGAAAATCATAAATA<br>AACAAGTGCTAGTATCAATATTTTTACCAAAAAATGGCATTCTTAGAATT<br>TTTTATAGGCTAGAAGGTTTGTACAAACTAATCTGCCACGGATTTTAAAA<br>TATGAGTGAATAAATTATATTGCAAAAAAAATCAGGTTACAGAGAACTGG<br>CAAGGAAGACTCTTATGTAAAACACAGAAAACATACAAAACGTATTTTTA<br>AGACAAATAAAAACAGAACTTGTACCTCAGATGATACTGGAGATTGTGTT<br>GACATATTAGCATTATCACTGTCTTGCTAAAACATAAAAATAAAAAGATG<br>GAAGATGAAATTACAATACAAATGATGATTTAAACATATAAAAGGAAAAT<br>AAAAATTGTTCTGACCAACTACTAAAGGAAGACCTACTAAAGATATGCCA<br>TCCAGCACATTGCCACTCTACATGTGGTCTGTAAACCAGCAGCATAGGCG<br>GCCGCATTAGC |
| Mouse c-myc 5MAR core<br>(SEQ ID NO: 29) | ATTCAACAGCTGAATCCTAAATTGCAAACTCAGTGGCTAATAACAACTTT<br>GAACAATGAGCACCTTATACACGCTACTGTATTTTCTTTTCTTTCTTTTT<br>TTTTTTTTTTTTTTTTTTTAAACCGGGTAGCAGTGAGAGAGGT |
| Mouse c-myc 5MAR 5'<br>flanking region (SEQ ID<br>NO: 30) | TGTAGTCATTTTGCAATCCTTAAAGCTGAATTGTGCAATGAGCTCGATGA<br>AGGAAGATACTATC |
| Mouse c-myc 5MAR core 3'<br>flanking region (SEQ ID<br>NO: 31) | TTCTTTAAGTGCCTTGGGGCGAGGAGTCCGGAATAAGAAGACTTCTTTGG<br>GTTTTAAAGTGTAGGATAAGCAA |
| Mouse c-myc 5MAR (SEQ ID<br>NO: 32) | AGCCCTGCCCCCATCCGACCTCCGCCCTCGTTGGCTTCGCAACGCTGTGG<br>TCTCTGTGGCCAGTAGAGGGCACACTTACTTTACTTTCACAAATCCGAGA<br>GCCACAACCCGGGTGGTGGGGGGTGAGGGGGCGGGGAAAGAGTCTCTGCA<br>GCAAAACGCAGACTAGGGATTGGTGGCTCTTGGTGTTTGAGGCAAAATCC<br>TAGAGGCTGTAGTCATTTTGCAATCCTTAAAGCTGAATTGTGCAATGAGC<br>TCGATGAAGGAAGATACTATCATTCAACAGCTGAATCCTAAATTGCAAAC<br>TCAGTGGCTAATAACAACTTTGAACAATGAGCACCTTATACACGCTACTG<br>TATTTTCTTTTCTTTCTTTTTTTTTTTTTTTTTTTTTTTTTTTAAACCGGGTA<br>GCAGTGAGAGAGGTTTCTTTAAGTGCCTTGGGGCGAGGAGTCCGGAATAA<br>GAAGACTTCTTTGGGTTTTAAAGTGTAGGATAAGCAAATCCCGAGGGAAT<br>ATGCATTATATAATAAATCTAGAACCAATGCACAGAGCAAAAGACTCATG<br>TTTCTGGTTGGTTAATAAGCTAGATTATCGTGTATATATAAAGTGTGTAT<br>GTATACGTTTGGGGATTGTACAGAATGCACAGCGTAGTATTCAGGAAAAA<br>GGAAACTGGGAAATTAATGTATAAATTAAAATCAGCTTTTAATTAGCTTA<br>ACACACACATACGAAGGCAAAAATGTAACGTTACTTTGATCTGATCAGGG<br>CCGACTTTTTTTTTTAAGTGCATAATTACGATTCCAGTAATAAAAGGGGA<br>AAGCTTGGGTTTGTCCTGGGAGGAAGGGGTTAACGGTTTTCTTTATTCTA<br>GGGTCTCTGCAGGCTCCCCAGATCTGGGTTGGCAATTCACTCCTCCCCCT<br>TTCTGGGAAGTCCGGGTTTTCCCCAACCCCCCAATTCATGGCATATTCTC<br>GCGTCTAGCGCCTTGATTTTCCCCACCCCAGCTCCTAAACCAGAGTCTGC<br>TGCAAACTGGCTCCACAGGGGCAAAGAGGATTTGCCTCTTGTGAAAACCG<br>ACTGTGGCCCTGGAACTGTGTGGAGGTGTATGGGGTGTAGACCGGCAGAG<br>ACTCCTCCCGGAGGAGCCGGGTAGAGCGCACCCGCCGCCACTTTACTGGA<br>CTGCGCAGGGAGACCTACAGGGGAAAGAGCGCGCCTCCACACCCACCCGCCG<br>GGTGGAAGTCCGAACCGGAGGTGCTGGAGTGTGTGTGTGGGGGGGGGGGG<br>GAATCTGCCTTTTGGCAGCAAATTGGGGGGGGGGGGTCGTTCTGGAAAGAA<br>TGTGCCCAGTCAACATAACTGTACGACCAAAGGCAAAATACACAATGCCT |

TABLE 1-continued

| MAR Sequences | |
|---|---|
| Name (SEQ ID NO:) | Sequence |
| | TCCCCGCGAGATGGAGTGGCTGTTTATCCCTAAGTGGCTCTCCAAGTATA<br>CGTGGCAGTGAGTTGCTGAGCAATTTTAATAAAATTCCAGACATCGTTTT<br>TCCTGCATAGACCTCATCTGCGGTTGATCACCCTCTATCACTCCACACAC<br>TGAGCGGGGGCTCCTAGATAACTCATTCGTTCGTCCTTCCCCCTTTCTAA<br>ATTCTGTTTTCCCCAGCCTTAGAGAGACGCCTGGCCGCCCGGGACGTGCG<br>TGACGCGGTCCAGGGTACATGGCGTATTGTGTGGAGCGAGGCAGCTGTTC<br>CACCTGCGGTGACTGATATACGCAGGGCAAGAACACAGTTCAGCCGA |
| SPR2A-MAR core (SEQ ID<br>NO: 33) | TCACAGACACTACAGAATGTTTTGGAGATTATGTAATATTTAAAATATTC<br>AAATTATACTAAAAATGTATGTAAAATGTATTGAACATAGGCAAGTTTCA<br>ATACATAGATTTTGAGTGAATGCTTGCAACTTTGGTTCCATTCTCT |
| SPR2A-MAR 5' flanking<br>region (SEQ ID NO: 34) | TCTGACTCTGCACTCTGCAACCTACTCTAATATTACATATGATAACATGA<br>GTCTATGCAGCTGTTCTCTATAGATAT |
| SPR2A-MAR core 3' flanking<br>region (SEQ ID NO: 35) | CTACTTCCTTAAGGTGGTGTCCAAGAGTACATTTTTATAAATAAAAAGTT<br>ATAGTACACTCCTAAGGGCAGCAAGTAGAAAACGTGCTAGGGAGACTCGA<br>TCTCACTTTG |
| SPR2A-MAR (SEQ ID NO: 36) | AAGCTTCCTTGGAATTAATGGTCAGATAAGGAGCTCTAGCAATATCACTT<br>TAAATGCTTAATATACAATATTTAGAAAACCTTATGATTGTAAAGAGCTT<br>AAAAAAGATGTGAAAGAACAATCACTAAAGCATTGACAACATATGTGTGT<br>TAGTGAACAATATGTACCAAAATGGACAGATGAGAGGTGTACATTGGGGT<br>GTGAGTTGATAATCCAGCAGACTGTGGGACTAGAGGGTCTACGAAAAACA<br>AAGGAAGAACATACAAACAAATTTTAAAACACTGTCTTTCAACACTAAAA<br>CTGTTGGAATAGAGAGCAAGAATACATATTGGATTCACATTCAGTTTATT<br>TCTCAGATTCAGACTAGTGCTCTGACTCTGCACTCTGCAACCTACTCTAA<br>TATTACATATGATAACATGAGTCTATGCAGCTGTTCTCTATAGATATTCA<br>CAGACACTACAGAATGTTTTGGAGATTATGTAATATTTAAAATATTCAAA<br>TTATACTAAAAATGTATGTAAAATGTATTGAACATAGGCAAGTTTCAATA<br>CATAGATTTTGAGTGAATGCTTGCAACTTTGGTTCCATTCTCTCTACTTC<br>CTTAAGGTGGTGTCCAAGAGTACATTTTTATAAATAAAAAGTTATAGTAC<br>ACTCCTAAGGGCAGCAAGTAGAAAACGTGCTAGGGAGACTCGATCTCACT<br>TTGGAATCTATCCTGGGAGACAAATGCCTCTACAAATGGATTAGAGAAGA<br>CAGTTTTAAAGAGGAAGATAATCAGGTAAAATCTGGGGTTTTATGAGAGA<br>AAGAAAGAGGTAGAAGAAAAAATTTCAAGCTCGAACATCGGATCAGGTGG<br>CACAATGCGGTCAATGCCTGCAAACTCAGGGTAAGTATTATTCTCCCTGT<br>TTACAGTTCCGTGGAGGAGAAGTGACTTGCCTGTGGTCATACAACAGAGC<br>AAAGAAAAGGCTTGAGCTAGAACTCAGGCCTTTGTTAGGTCTCCCCTTCC<br>TCCTAGCACATTGGCAAATTGCATGAGGAAAGTAGAGGTACAGTTGAGTT<br>CATGTACAACAATAAGGCATTCAGGTAAAGTGAATGAGGGCAGAAGTTTT<br>ATGATTTAGGGAAGGTGTAAGACAGGAAAATATCTTTGTTCCCAATTAAG<br>AAAGAGATCCCTTGACCATCAGTTAGAGATTCCCCCAAGTCCCTCTTTGC<br>CATAAGTCACTGAAACTGAGATCCAAGGCATGGCTTCTGTGAGTCAGGAG<br>AGCTTAACCCAGAGGAGAGATTTCAGAACAGGATATTTCCTATTTTGAGT<br>ATCCTGCTCATGCCAGTCATGGATAAATTTGCATCTGGCTTAAGAAATTA<br>CTGGATCAGCATTGTTTTGGGTAGTTTCACTTCCTGCTGGGTGGGGTAGC<br>AGGCTCTATAAAGAGATCCTCTGCTGCACGACTCTTAAACCCCTGGTACC<br>TGAGCACTGATCTGCCTTGGAGAACCTGGTGAGTCGGCTTCCTTGAGTTC<br>CTCTGTTCTTTGTGCCCTGAAATGTTGAGTTTAATCTGAATATGGCAAGT<br>TTGGTGGATCCAATCCTATGAAAATTGACTTGATGCTACTTAGTGGATGA<br>AAATTTAAGATTAGAGCACAATTATATGCTATTTTAGCTTTCTTTTGTTA<br>TACAGGTAGGTATCCATATGGACAGAGAAGTTAAGGGGTAACCTTTGATA<br>TGAAGAAGAAAAAAGAACAAAGTATTTTTCTTTATTCTCTTGCTTTCTAG<br>TGTCCTTTACAAAGGTTTGTGTCTTAGCAGGTGTGAAAGACTACAATTCT<br>CCCTGAGCAGCCCTTTGCTCTATGCCCAAGTCAGCCCACTTGGACTTTAT<br>AACAGATAATGATGATAGGAATAGCATATTAGATTGCCCAGGGTGTCTGA<br>ACTTGTGACTGCCTTTCTTGAATTGGTTATTTTCAGGGAAATAAGATGCT<br>TGATTCTTTATAACAGAGATAATTTATTTGGAAAAATTGTATGAGAAAAC<br>ACAGGATTTCCTAGGGACAATGAAGCAATTTGTTAAAGTGGAAGGGAGAA<br>ACCAGAAAGTCTTGAAAAGGTAATTAAGAATTTAAATAATTTCTTGGAGA<br>TTGGAGAAATAATATGCCATGGTATTACACAAGCTTTGGCTTCTCTCTCT<br>GGAGGATTCCCTTCCCACGAACACTGTTGTATCATTTCTTTCAGA |

Note:
in full-length sequences, the core regions are bold and underlined, and the flanking regions are
underlined.

Example 2. Testing of MAR Zebrafish

Experimental testing of one of the identified MAR elements, MAR Zebrafish, was conducted in comparison to the strongest known MAR from literature and was shown to be two times more potent.

In vitro comparison was made between MAR Zebrafish, a newly identified MAR element, and MAR X29 (reference, see Arope et al. (2013) PLoS ONE 8(11): e79262).

Experimental testing of the MAR Zebrafish core, which did not include the flanking regions of the full-length MAR Zebrafish, was then conducted in comparison to a construct that did not contain any MAR sequences.

Methods and Materials

Neon transfection was done with CT MCB cells. BalanCD+4 mM Gln Media was used for transfection. Transient Transfection done by Bio-Rad: Gene Pulser II setting at 900 uF, 300 v resistance 0. Cells were split before 24 hours of transfection. Day 0 viability & VCD are measured as million cells/ml. Transfections were done using 5 µg of Heavy Chain & Light chain DNA. 10 µg of GFP DNA was used as an external control to check the transfection efficiency. Stable pools were generated by maintaining methionine sulfoximine (MSX) at levels resulting in selective pressure that favored the growth of cells expressing the recombinant protein of interest, Rituximab Light Chain, for 14 days. Resulting recombinant pools were compared in 14 day fed batch quantitation assays. Titers at the day of harvest and throughout culture were analyzed by biolayer interferometry or ELISA. The experimental method above for pool generation was repeated to generate the pools for testing the MAR Zebrafish core, using only one concentration of MSX, 80 µM.

Results

The results of the in vitro comparison of MAR X29 and MAR Zebrafish are shown in FIG. 1. At both selection marker concentrations (methionine sulfoximine (MSX) at 8004 and 100 µM), MAR Zebrafish outperformed MAR X29 by a considerable margin. This example, therefore, validated the search and in silico approach developed in Example 1.

Figure 2:
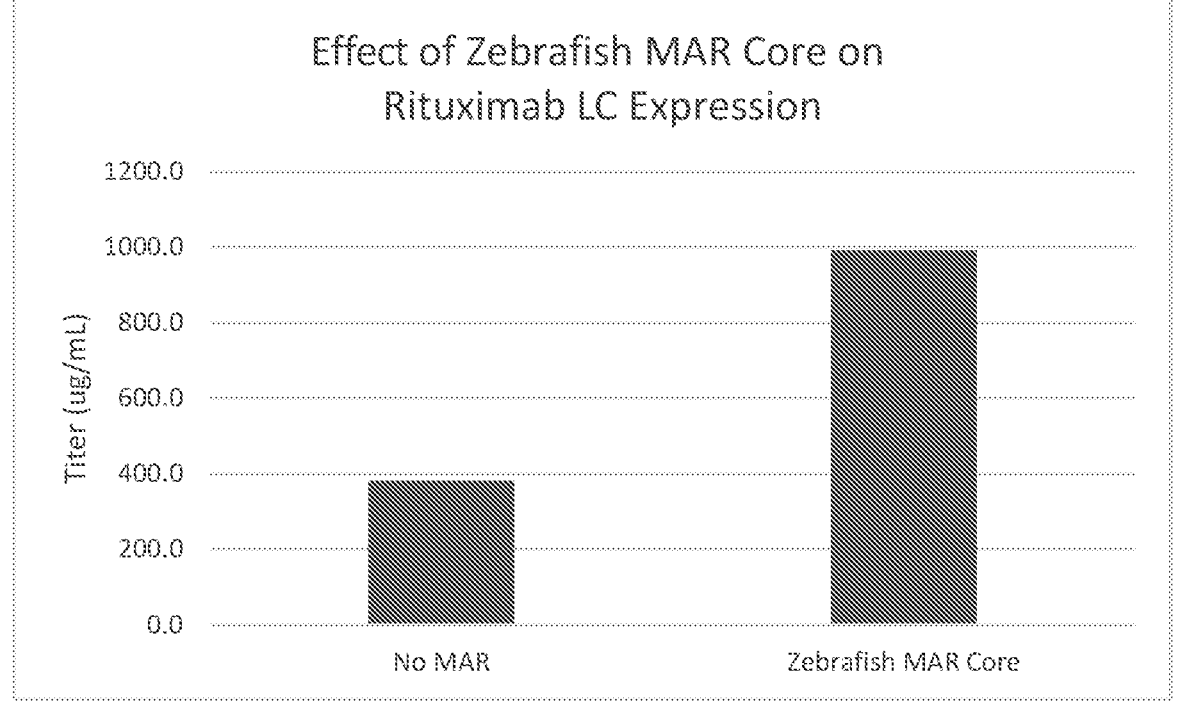
FIG. 2 demonstrates the strength of the MAR Zebrafish core using as control a construct that does not contain any MAR sequences.
Figure 3:
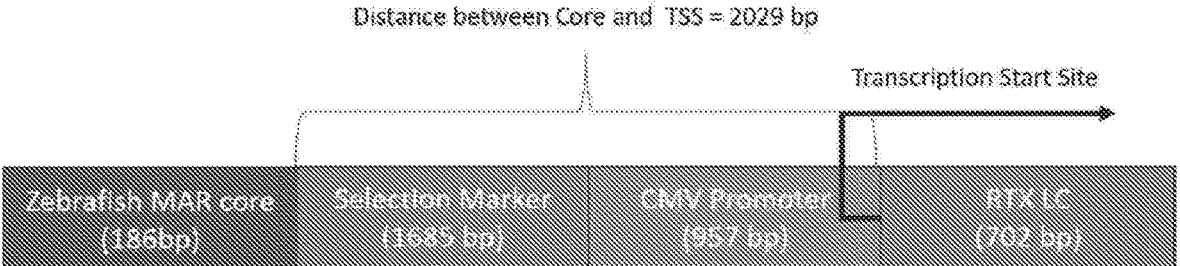
FIG. 3 is the vector map of a MAR core-containing construct described in Example 2.
Figure 4:
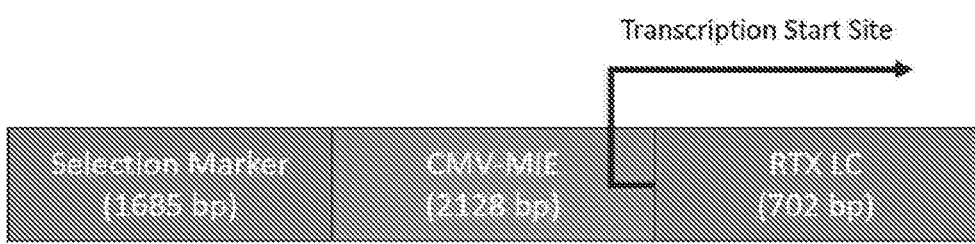
FIG. 4 is the vector map of the control construct that did not contain the MAR core element, as described in Example 2.

In a further experiment, the potency of the MAR core sequence alone was tested in comparison to a construct without any MAR elements. As shown in FIG. 2, The MAR Zebrafish core sequence resulted in significantly higher titers than the no MAR control.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

What is claimed is:

1. An engineered recombinant expression cassette on the same polynucleotide consisting of (i) a heterologous promoter operably linked to (ii) a coding sequence encoding a transgene to initiate the transcription of the coding sequence, and (iii) a matrix attachment region (MAR) nucleic acid sequence comprising SEQ ID NO: 1 or SEQ ID NO:4, wherein the MAR is capable of attaching to a mammalian nuclear matrix and enhancing gene expression in cells; wherein the heterologous promoter is not naturally associated with the MAR sequence in its native genomic context.

2. A cell comprising the engineered recombinant expression cassette of claim 1, wherein the engineered recombinant expression cassette is heterologous to said cell.

* * * * *